United States Patent
Weichert et al.

(10) Patent No.: US 11,186,598 B2
(45) Date of Patent: *Nov. 30, 2021

(54) RADIOACTIVE PHOSPHOLIPID METAL CHELATES FOR CANCER IMAGING AND THERAPY

(71) Applicant: Wisconsin Alumni Research Foundation, Madison, WI (US)

(72) Inventors: Jamey Weichert, Sun Prairie, WI (US); Anatoly Pinchuk, Fitchburg, WI (US); Reinier Hernandez, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/891,181

(22) Filed: Jun. 3, 2020

(65) Prior Publication Data

US 2020/0291049 A1 Sep. 17, 2020

Related U.S. Application Data

(62) Division of application No. 15/343,604, filed on Nov. 4, 2016, now abandoned.

(60) Provisional application No. 62/366,344, filed on Jul. 25, 2016.

(51) Int. Cl.
| | |
|---|---|
| *A61K 51/00* | (2006.01) |
| *A61M 36/14* | (2006.01) |
| *C07F 9/6524* | (2006.01) |
| *C07B 59/00* | (2006.01) |
| *G01N 33/574* | (2006.01) |
| *A61K 51/04* | (2006.01) |
| *A61N 5/10* | (2006.01) |
| *G01N 33/60* | (2006.01) |

(52) U.S. Cl.
CPC ........ *C07F 9/6524* (2013.01); *A61K 51/0482* (2013.01); *A61K 51/0489* (2013.01); *A61N 5/10* (2013.01); *C07B 59/004* (2013.01); *G01N 33/574* (2013.01); *G01N 33/60* (2013.01)

(58) Field of Classification Search
None
See application file for complete search history.

(56) References Cited

U.S. PATENT DOCUMENTS

| | | | |
|---|---|---|---|
| 10,265,398 B2 * | 4/2019 | Weichert | C07F 9/11 |
| 10,813,998 B2 * | 10/2020 | Weichert | A61P 35/00 |

\* cited by examiner

*Primary Examiner* — Michael G. Hartley
*Assistant Examiner* — Melissa J Perreira
(74) *Attorney, Agent, or Firm* — Boyle Fredrickson S.C.

(57) ABSTRACT

Alkylphosphocholine analogs incorporating a chelating moiety that chelates a radioactive metal isotope are disclosed herein. The alkylphophocholine analogs, which can be used to treat or detect solid tumors, have the formula:

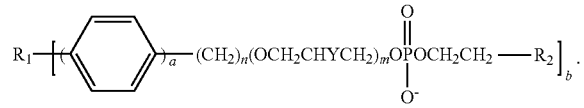

$R_1$ includes a chelating agent that is chelated to a metal atom, wherein the metal atom is a positron or single photon emitting metal isotope with a half life of greater than or equal to 4 hours, or an alpha, beta or Auger emitting metal isotope with a half life of greater than 6 hours and less than 30 days; a is 0 or 1; n is an integer from 12 to 30; m is 0 or 1; Y is —H, —OH, —COOH, —COOX, —OCOX, or —OX, wherein X is an alkyl or an arylalkyl; $R_2$ is —$N^+H_3$, —$N^+H_2Z$, —$N^+HZ_2$, or —$N^+Z_3$, wherein each Z is independently an alkyl or an aroalkyl; and b is 1 or 2.

19 Claims, 19 Drawing Sheets

RADIOACTIVE PHOSPHOLIPID METAL CHELATES FOR CANCER IMAGING AND THERAPY

CROSS-REFERENCE TO RELATED APPLICATIONS

This application is a divisional of U.S. application Ser. No. 15/343,604 filed Nov. 4, 2016, which claims the benefit of U.S. provisional Application No. 62/366,344 filed on Jul. 25, 2016. Each of these applications is incorporated by reference herein in its entirety.

STATEMENT REGARDING FEDERALLY SPONSORED RESEARCH OR DEVELOPMENT

Not applicable.

FIELD OF THE DISCLOSURE

This disclosure relates generally to disease treatment and medical diagnosis/imaging. In particular, the disclosure is directed to the alkylphosphocholine analogs that include chelated radioactive metal isotopes to target and treat a wide range of pediatric and adult malignant solid tumors, and to detect/image malignant solid tumor cells.

BACKGROUND

There are currently a variety of radiopharmaceuticals available for tumor imaging, but these are limited by non-specificity for malignancy, the inability to distinguish cancer from inflammation, short biological half-life, and generally poor spatial resolution associated with PET and SPECT scanning modalities.

We have previously shown that certain alkylphosphocholine analogs are preferentially taken up and retained by malignant solid tumor (i.e., solid tumor cancer) cells. In U.S. Patent Publication No. 2014/0030187, which is incorporated by reference herein in its entirety, Weichert et al. disclose using analogs of the base compound 18-(p-iodophenyl) octadecyl phosphocholine (NM404; see FIG. 1) for detecting and locating, as well as for treating, a wide variety of solid tumor cancers. For example, if the iodo moiety is an imaging-optimized radionuclide, such as iodine-124 ($[^{124}I]$-NM404), the analog can be used in positron emission tomography-computed tomography (PET/CT) or single-photon emission computed tomography (SPECT) imaging of adult solid tumors. Alternatively, if the iodo moiety is a radionuclide optimized for delivering therapeutic doses of radiation to the solid tumors cells in which the analog is taken up, such as iodine-125 or iodine-131 ($[^{125}I]$-NM404 or $[^{131}I]$-NM404), the analog can be used to treat solid tumors.

There are a few recognized issues with using compounds that include radioactive iodine isotopes for targeted radiation cancer therapy and/or imaging. For example, I-124, suffers from poor positron output (only about 24% of the emissions are positrons), and it suffers further from a confounding gamma emission (600 KeV) which actually interferes with normal 511 keV PET detection. Iodine-131, as a radiotherapy isotope, also contains other emissions at other energies, which add undesired radiation dosimetry to neighboring normal tissues, including bone marrow. The beta particle range of I-131 is also quite long, which contributes to off target toxicity.

Accordingly, there is a need in the art for improved cancer targeting agents for use in targeted cancer radiation therapy and/or imaging applications.

BRIEF SUMMARY

The current disclosure provides new radioactive phospholipid metal chelates that can be used as improved cancer imaging and/or radiotherapy agents. A variety of positron- and gamma-emitting metals suitable for PET or SPECT imaging are available for chelation, as well as a variety of α-, β-, and Auger-emitting metal nuclides for targeted radiotherapy. For either imaging or radiotherapy, radioactive metal isotopes with a minimum physical decay half-life of 6 h are necessary, due to the pharmacokinetic profile of the molecular carrier.

The radiactive phospholipid metal chelate compounds disclosed herein utilize an alkyl-phospholipid carrier combined with one of a variety of metal chelators that is chelated to a radioactive metal isotope. Although radioiodinated versions have been shown to target cancer cells in vivo, the disclosed metallic chelates are structurally quite different. Specifically, they have a different charge, much larger size, and more lipophilic chemical properties. Despite these differences, the disclosed chelates exhibit formulation properties that render them suitable for injection and possess suitable in vivo stability, while retaining tumor selectivity.

The disclosed metal chelates are preferentially taken up by malignant solid tumor cells, as compared to non-tumor cells. Preferential uptake of such compounds can be used in the therapeutic treatment of malignant solid tumors, as well as in malignant solid tumor detection/imaging applications. In therapeutic treatment, the alkylphosphocholine targeting backbone includes a chelated radioactive metal isotope that locally delivers therapeutic dosages of radiation to the malignant solid tumor cells that preferentially take up the metal chelates. In detection/imaging applications, the alkylphosphocholine targeting backbone includes a chelated radioactive metal isotope suitable for emitting signals that can be used in detection/imaging.

Accordingly, the disclosure encompasses a family of radioactive phospholipid metal chelate compounds, compounds that can be used as cancer imaging agents and/or therapeutic agents for targeted cancer radiotherapy.

In a first aspect, the disclosure encompasses a compound having the formula:

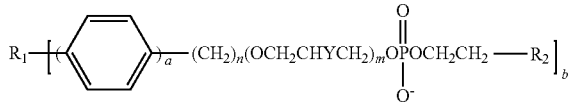

or a salt thereof $R_1$ includes or is a chelating agent that is chelated to a metal atom, wherein the metal atom is a positron or single photon emitting metal isotope with a half life of greater than or equal to 4 hours, or an alpha, beta or Auger emitting metal isotope with a half life of greater than 6 hours and less than 30 days; a is 0 or 1; n is an integer from 12 to 30; m is 0 or 1; Y is —H, —OH, —COOH, —COOX, —OCOX, or —OX, wherein X is an alkyl or an arylalkyl; $R_2$ is —$N^+H_3$, —$N^+H_2Z$, —$N^+HZ_2$, or —$N^+Z_3$, wherein each Z is independently an alkyl or an aroalkyl; and b is 1 or 2.

In some embodiments, the metal atom is a positron or single photon emitting metal isotope with a half life of greater than or equal to 4 hours. Such isotopes are particularly suited for use in imaging applications. Non-limiting examples of such isotopes include Ga-66, Cu-64, Y-86, Co-55, Zr-89, Sr-83, Mn-52, As-72, Sc-44, Ga-67, In-111, and Tc-99m.

In some embodiments, the metal atom is an alpha, beta or Auger emitting metal isotope with a half life of greater than 6 hours and less than 30 days. Such isotopes are particularly suited for use in targeted radiotherapy applications. Non-limiting examples of such isotopes include Lu-177, Y-90, Ho-166, Re-186, Re-188, Cu-67, Au-199, Rh-105, Ra-223, Ac-225, As-211, Pb-212, and Th-227.

In some embodiments, the chelating agent is 1,4,7,10-tetraazacyclododecane-1,4,7-triacetic acid (DO3A) or one of its derivatives; 1,4,7-triazacyclononane-1,4-diacetic acid (NODA) or one of its derivatives; 1,4,7-triazacyclononane-1,4,7-triacetic acid (NOTA) or one of its derivatives; 1,4,7,10-tetraazacyclododecane-1,4,7,10-tetraacetic acid (DOTA) or one of its derivatives; 1,4,7-triazacyclononane, 1-glutaric acid-4,7-diacetic acid (NODAGA) or one of its derivatives; 1,4,7,10-tetraazacyclodecane, 1-glutaric acid-4,7,10-triacetic acid (DOTAGA) or one of its derivatives; 1,4,8,11-tetraazacyclotetradecane-1,4,8,11-tetraacetic acid (TETA) or one of its derivatives; 1,4,8,11-tetraazabicyclo[6.6.2]hexadecane-4,11-diacetic acid (CB-TE2A) or one of its derivatives; diethylene triamine pentaacetic acid (DTPA), its diester, or one of its derivatives; 2-cyclohexyl diethylene triamine pentaacetic acid (CHX-A"-DTPA) or one of its derivatives; deforoxamine (DFO) or one of its derivatives; 1,2-[[6-carboxypyridin-2-yl]methylamino]ethane (H$_2$dedpa) or one of its derivatives; or DADA or one of its derivatives, wherein DADA has the structure:

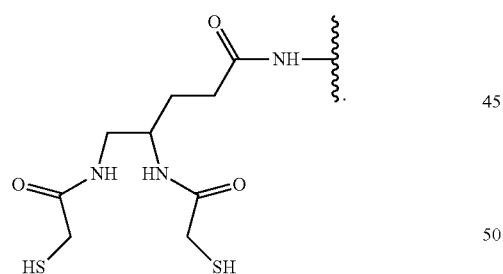

In some embodiments, a is 1 (aliphatic aryl-alkyl chain). In other embodiments, a is 0 (aliphatic alkyl chain).

In some embodiments, m is 1 (acylphospholipid series).

In some embodiments, n is an integer between 12 and 20.

In some embodiments, Y is —OCOX, —COOX or —OX. In some such embodiments, X is —CH$_2$CH$_3$ or —CH$_3$.

In some embodiments, m is 0 (alkylphospholipid series).

In some embodiments, b is 1.

In some embodiments, n is 18.

In some embodiments, R$_2$ is —N$^+$Z$_3$. In some such embodiments, each Z is independently —CH$_2$CH$_3$ or —CH$_3$. In some such embodiments, each Z is —CH$_3$.

Non-limiting examples of the chelating agent that can be chelated to the metal atom include:

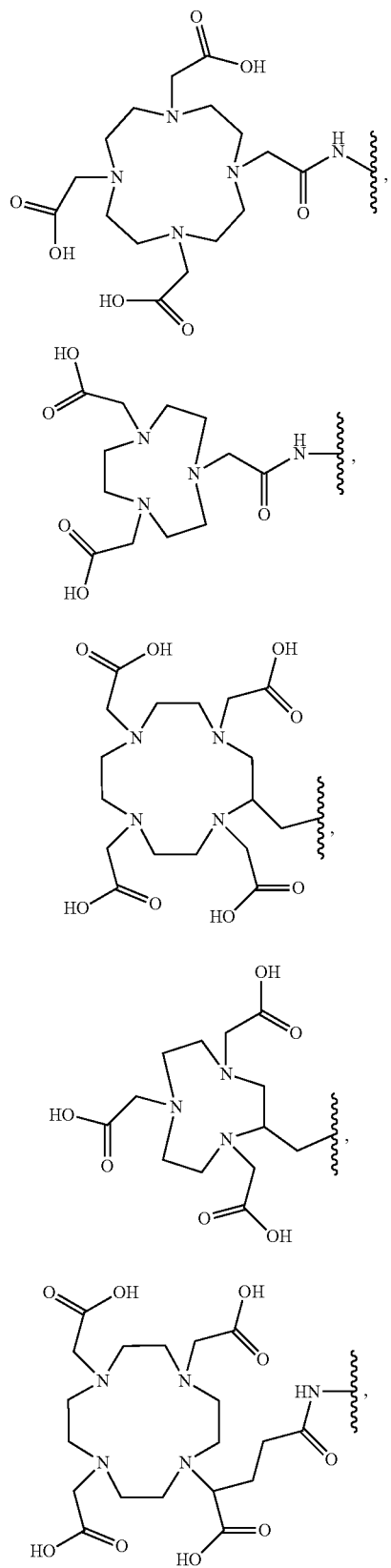

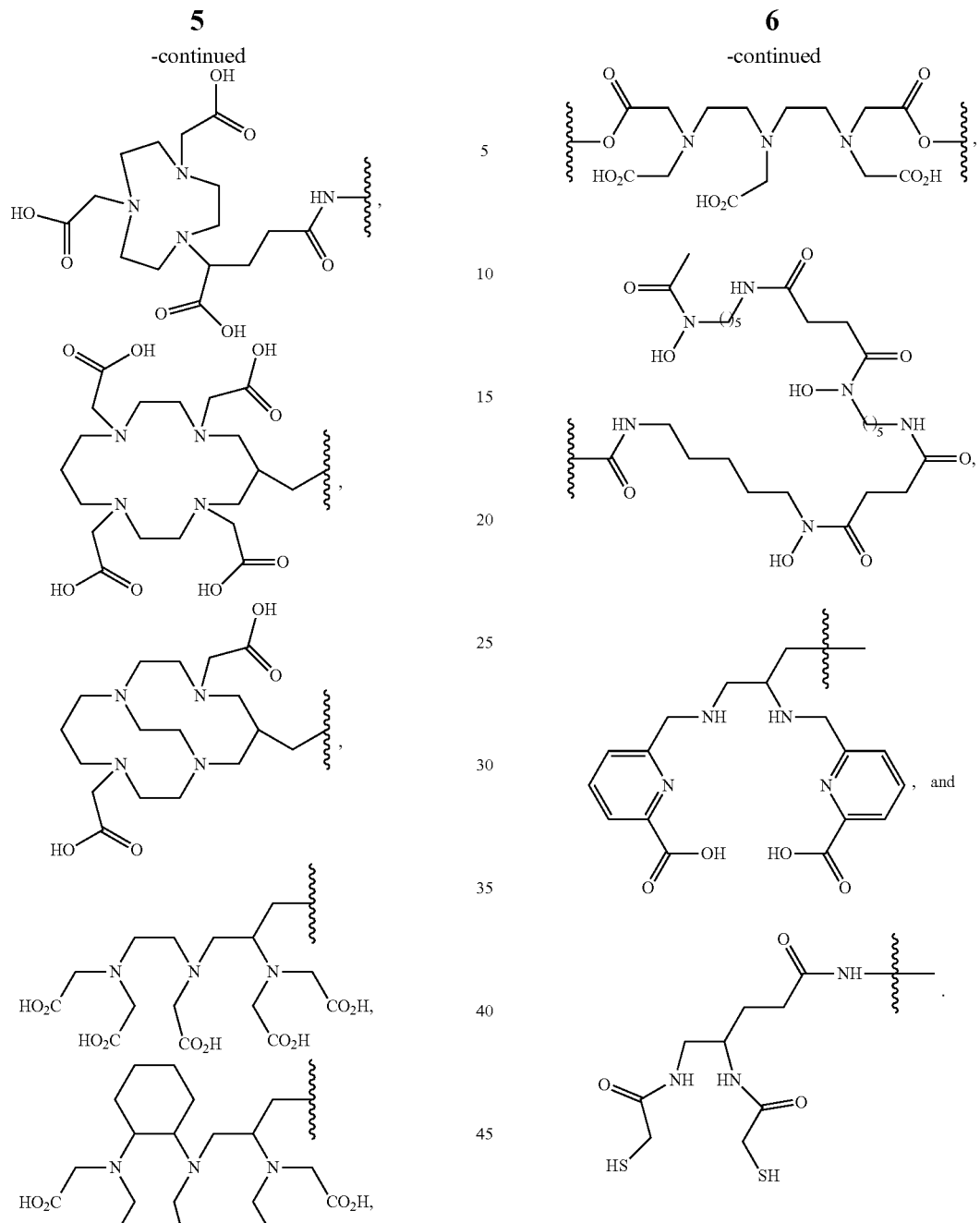
Non-limiting examples of the disclosed cancer imaging and/or therapeutic agents include:
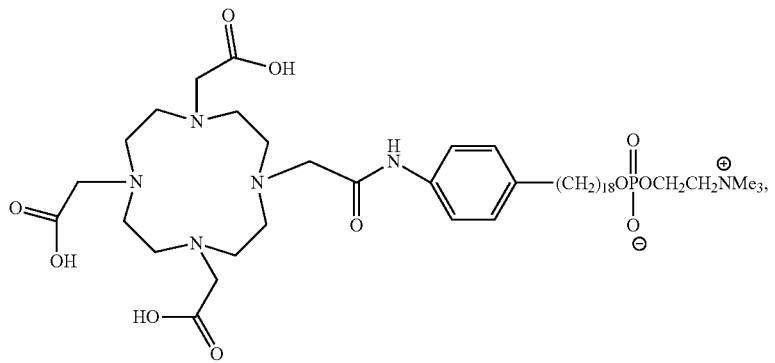

-continued
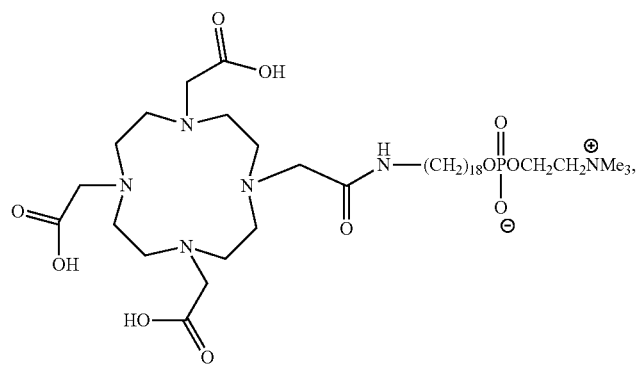
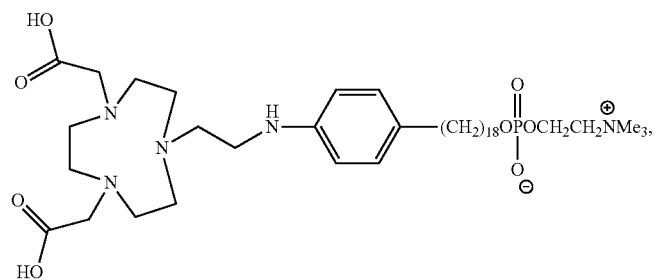
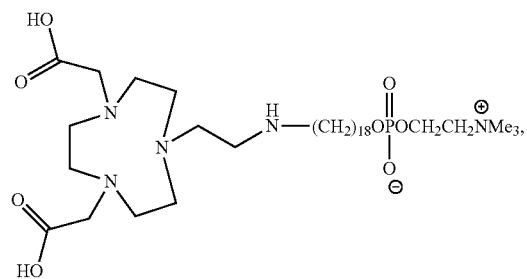
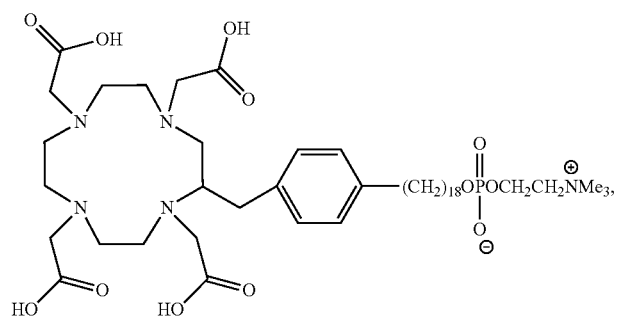
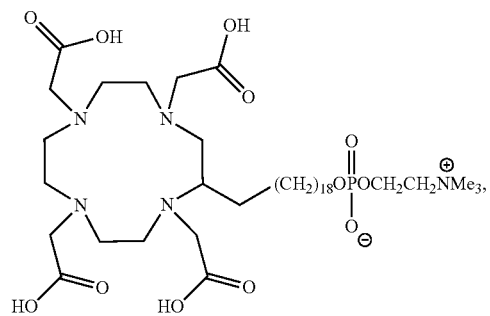

-continued
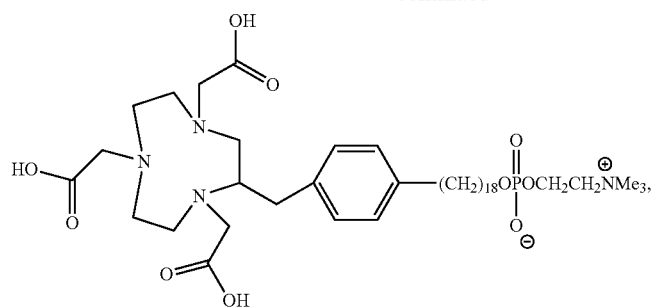
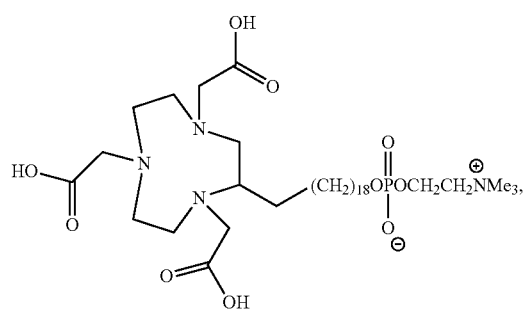
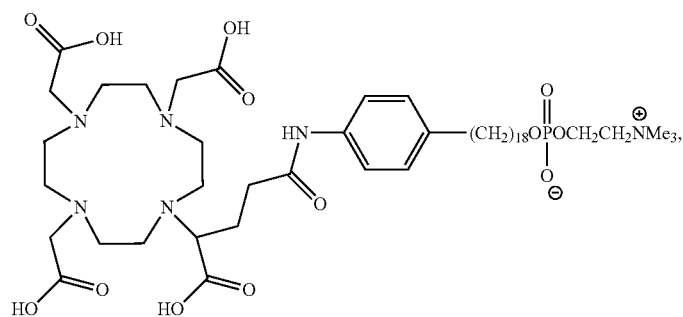
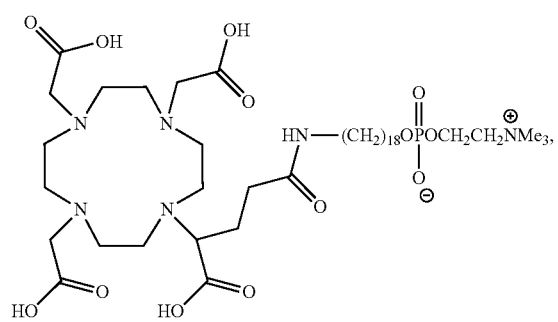
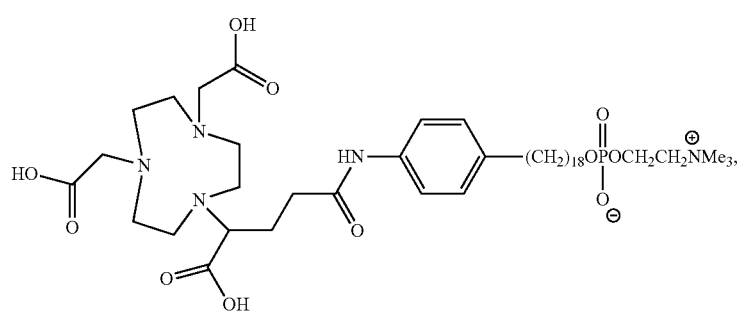

-continued
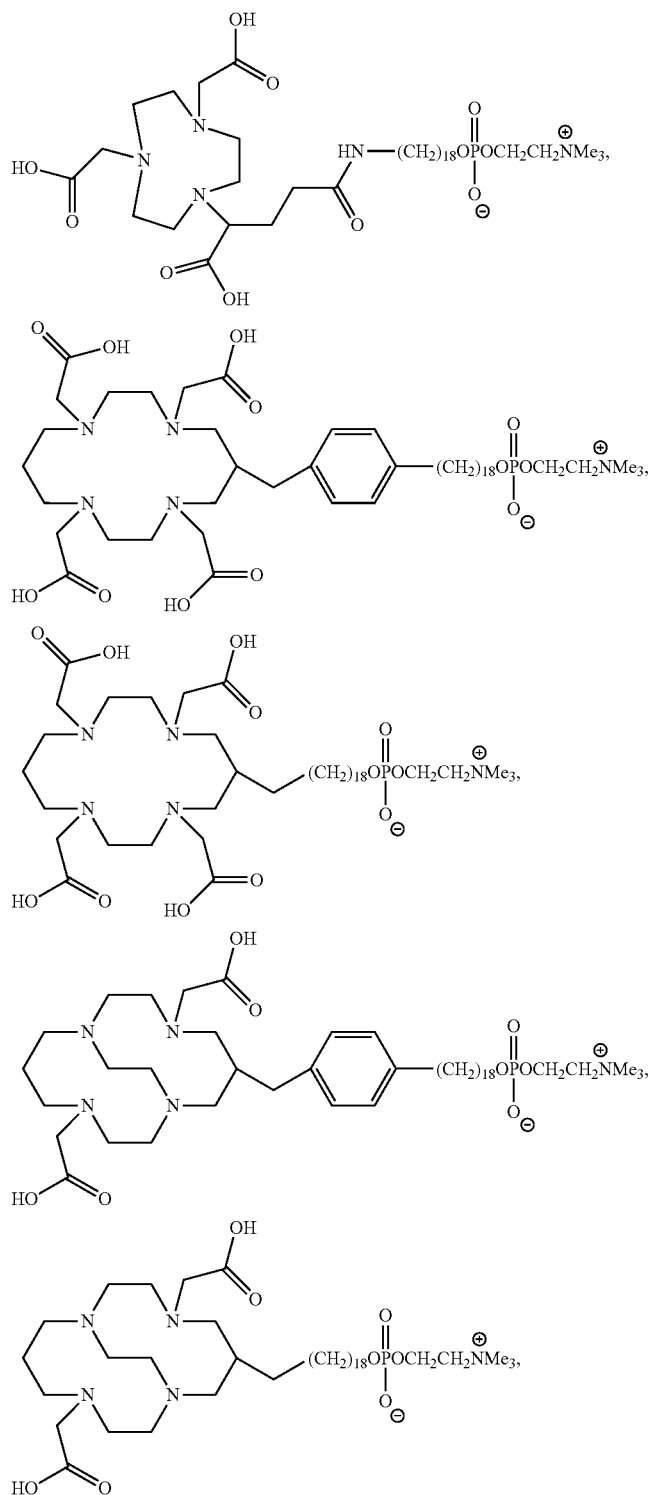
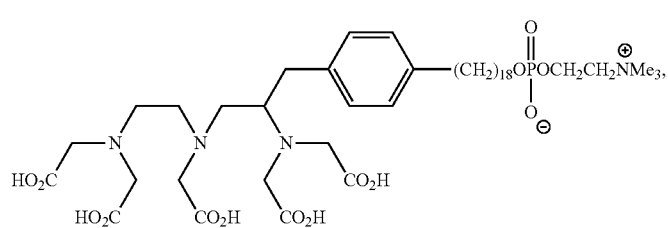

-continued
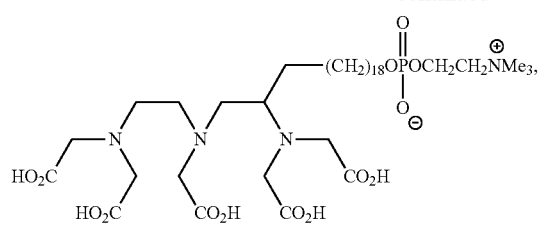
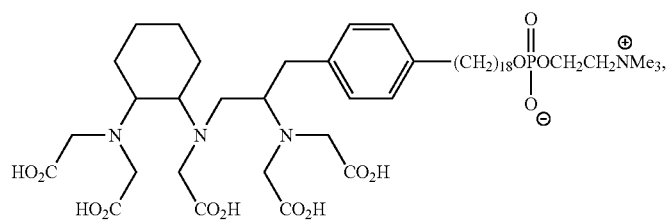
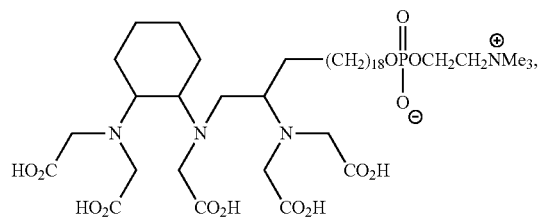
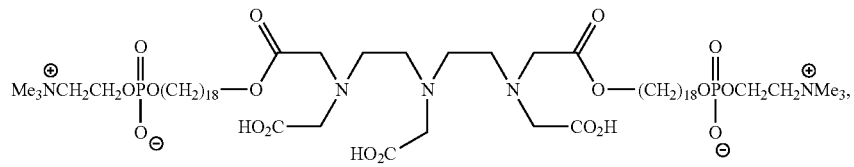
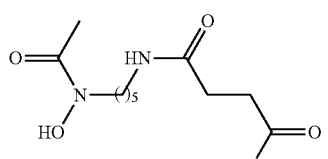
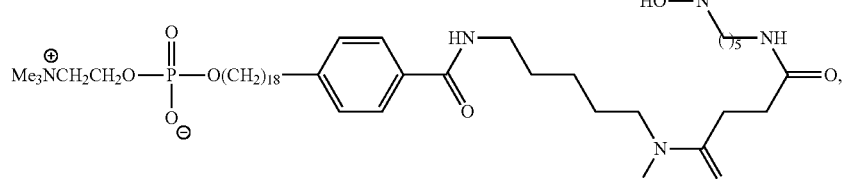
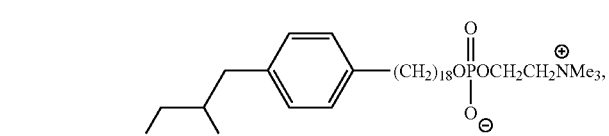
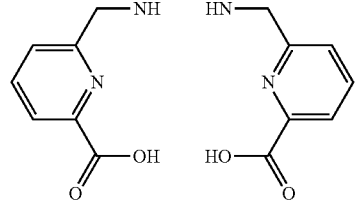

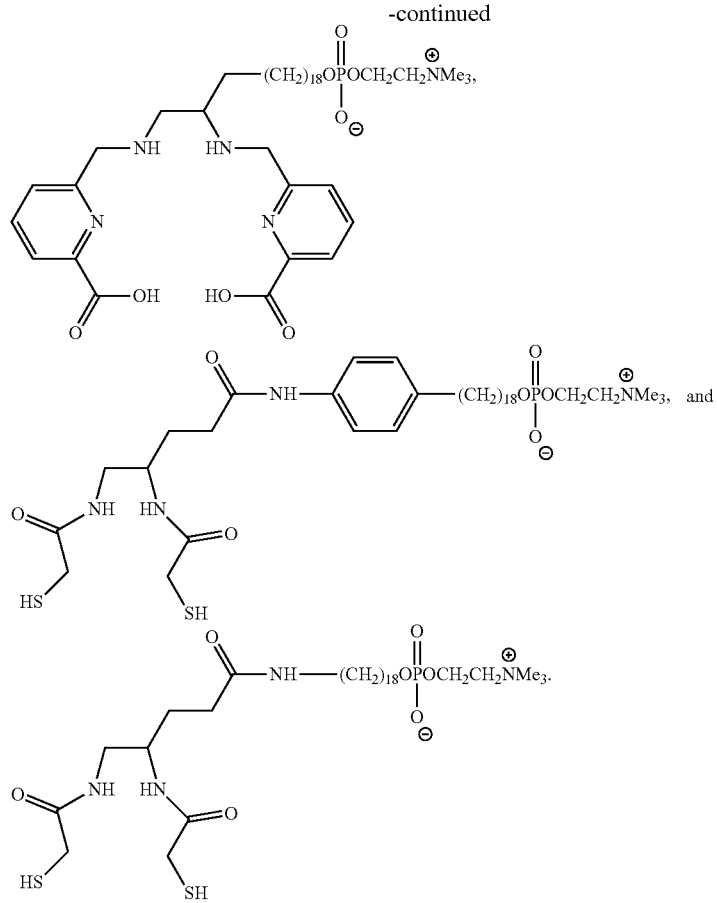

In each case, the exemplary compound is chelated to the metal atom.

In a second aspect, the disclosure encompasses a composition that includes one or of the compounds described above, and a pharmaceutically acceptable carrier.

In a third aspect, the disclosure encompasses one or more of the compounds described above for use in imaging cancer or cancerous cells.

In a fourth aspect, the disclosure encompasses one or more of the compounds described above for use in treating cancer.

In a fifth aspect, the disclosure encompasses one or more of the compounds described above for use in treating cancer for use in manufacturing a medicament for treating or imaging cancer.

In a sixth aspect, the disclosure encompasses a method for treating a cancer in a subject. The method includes the step of administering to a subject having cancer an effective amount of one or more of the compounds described above, wherein the metal atom is an alpha, beta or Auger emitting metal isotope with a half life of greater than 6 hours and less than 30 days.

In some embodiments of the method, the chelated metal isotope is Lu-177, Y-90, Ho-166, Re-186, Re-188, Cu-67, Au-199, Rh-105, Ra-223, Ac-225, As-211, Pb-212, or Th-227.

In some embodiments, the compound is administered by parenteral, intranasal, sublingual, rectal, or transdermal delivery. In some such embodiments, the compound is administered intravenously. In some embodiments, the compound is administered intratumoraly.

In some embodiments, the subject is a human.

In some embodiments, the cancer that is treated is an adult solid tumor or a pediatric solid tumor. Non-limiting examples of cancers that could be treated include melanoma, neuroblastoma, lung cancer, adrenal cancer, colon cancer, colorectal cancer, ovarian cancer, prostate cancer, liver cancer, subcutaneous cancer, squamous cell cancer, intestinal cancer, retinoblastoma, cervical cancer, glioma, breast cancer, pancreatic cancer, Ewings sarcoma, rhabdomyosarcoma, osteosarcoma, retinoblastoma, Wilms' tumor, and pediatric brain tumors.

In a seventh aspect, the disclosure encompasses a method for inhibiting the proliferation or growth of malignant cells. The method includes the step of contacting one or more malignant cells with an effective amount of one or more of the compounds described above, wherein the metal atom is an alpha, beta or Auger emitting metal isotope with a half life of greater than 6 hours and less than 30 days.

Non-limiting examples of metal isotopes that could be used include Lu-177, Y-90, Ho-166, Re-186, Re-188, Cu-67, Au-199, Rh-105, Ra-223, Ac-225, As-211, Pb-212, and Th-227.

In some embodiments, the method is performed in vivo, ex vivo, or in vitro.

In some embodiments, the malignant cells are adult solid tumor cells or pediatric solid tumor cells. Non-limiting examples of such cells include melanoma cells, neuroblastoma cells, lung cancer cells, adrenal cancer cells, colon cancer cells, colorectal cancer cells, ovarian cancer cells, prostate cancer cells, liver cancer cells, subcutaneous cancer cells, squamous cell cancer cells, intestinal cancer cells, retinoblastoma cells, cervical cancer cells, glioma cells, breast cancer cells, pancreatic cancer cells, Ewings sarcoma cells, rhabdomyosarcoma cells, osteosarcoma cells, retinoblastoma cells, Wilms' tumor cells, and pediatric brain tumor cells.

In an eighth aspect, the disclosure encompasses a method for detecting or imaging one or more cancer cells in a biological sample. The method includes the steps of (a) contacting the biological sample with one or more of the compounds described above, wherein the metal atom is a positron or single photon emitting metal isotope with a half life of greater than or equal to 4 hours, whereby the compound is differentially taken up by malignant solid tumor cells within the biological sample; and (b) identifying individual cells or regions within the biological sample that are emitting signals characteristic of the metal isotope.

Non-limiting examples of metal isotopes that could be used include Ga-66, Cu-64, Y-86, Co-55, Zr-89, Sr-83, Mn-52, As-72, Sc-44, Ga-67, In-111, and Tc-99m.

In some embodiments, the step of identifying individual cells or regions within the biological sample that are emitting signals characteristic of the metal isotope is performed by positron emission tomography (PET) imaging, single-photon emission computed tomography (SPECT) imaging, or gamma camera planar imaging.

In some embodiments, the biological sample is part or all of a subject.

In some embodiments, the biological sample is obtained from a subject.

In some embodiments, the subject is a human.

In some embodiments, the cancer cells are adult solid tumor cells or pediatric solid tumor cells. Non-limiting examples of such cells include melanoma cells, neuroblastoma cells, lung cancer cells, adrenal cancer cells, colon cancer cells, colorectal cancer cells, ovarian cancer cells, prostate cancer cells, liver cancer cells, subcutaneous cancer cells, squamous cell cancer cells, intestinal cancer cells, retinoblastoma cells, cervical cancer cells, glioma cells, breast cancer cells, pancreatic cancer cells, Ewings sarcoma cells, rhabdomyosarcoma cells, osteosarcoma cells, retinoblastoma cells, Wilms' tumor cells, and pediatric brain tumor cells.

In a ninth aspect, the disclosure encompasses a method of diagnosing cancer in a subject. The method includes one or more of the imaging/detection steps outlined above. In the method, the biological sample is obtained from, part of, or all of a subject. If cancer cells are detected or imaged in the method steps, the subject is diagnosed with cancer.

In some embodiments, the cancer that is diagnosed is an adult solid tumor or a pediatric solid tumor. Non-limiting examples of such cancer include melanoma, neuroblastoma, lung cancer, adrenal cancer, colon cancer, colorectal cancer, ovarian cancer, prostate cancer, liver cancer, subcutaneous cancer, squamous cell cancer, intestinal cancer, retinoblastoma, cervical cancer, glioma, breast cancer, pancreatic cancer, Ewings sarcoma, rhabdomyosarcoma, osteosarcoma, retinoblastoma, Wilms' tumor, and pediatric brain tumors.

In a tenth aspect, the disclosure encompasses a method of monitoring the efficacy of a cancer therapy in a human subject. The method includes performing one or more of the imaging/detection steps outlined above at two or more different times on the biological sample, wherein the biological sample is obtained from, part of, or all of a subject. The change in strength of the signals characteristic of the metal isotope between the two or more different times is correlated with the efficacy of the cancer therapy.

In some embodiments, the cancer therapy being monitored is chemotherapy or radiotherapy.

In an eleventh aspect, the disclosure encompasses a method of treating cancer in a subject. The method includes performing one or more of the imaging/detection steps outlined above, wherein the biological sample is part of or all of a subject. The method also includes the step of directing an external radiotherapy beam to the identified individual cells or regions within the subject.

Other objects, features and advantages of the present invention will become apparent after review of the specification, claims and drawings.

BRIEF DESCRIPTION OF THE DRAWINGS

FIG. 7 includes T1-weighted SPGR MR images obtained before the contrast agent is injected. The locations of the myocardium (M, top image), liver (L, center image), and kidney (K, bottom image) are indicated by arrows, and are consistent with the corresponding images shown in FIGS. 9-12.

FIG. 8 includes T1-weighted SPGR MR images obtained one hour after Gd-DO3A-404 contrast agent is injected. The images include the myocardium (top image), liver (center image), and kidney (bottom image).

FIG. 9 includes T1-weighted SPGR MR images obtained 24 hours after Gd-DO3A-404 contrast agent is injected. The images include the myocardium (top image), liver (center image), and kidney (bottom image).

FIG. 10 includes T1-weighted SPGR MR images obtained four days after Gd-DO3A-404 contrast agent is injected. The images include the myocardium (top image), liver (center image), and kidney (bottom image).

FIG. 11 includes T1-weighted SPGR MR images obtained seven days after Gd-DO3A-404 contrast agent is injected. The images include the myocardium (top image), liver (center image), and kidney (bottom image).

DETAILED DESCRIPTION

I. In General

Figure 1:
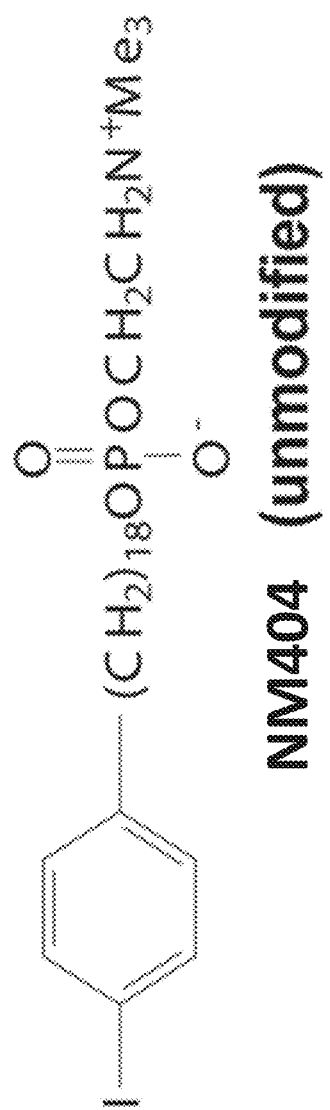
FIG. 1 shows the chemical structure of the base compound 18-(p-iodophenyl)octadecyl phosphcholine (NM404).

It is understood that this disclosure is not limited to the particular methodology, protocols, materials, and reagents described, as these may vary. The terminology used herein is for the purpose of describing particular embodiments only, and is not intended to limit the scope of the present invention, which will be limited only by any later-filed nonprovisional applications.

As used herein and in the appended claims, the singular forms "a", "an", and "the" include plural reference unless the context clearly dictates otherwise. As well, the terms "a" (or "an"), "one or more" and "at least one" can be used interchangeably herein. The terms "comprising" and variations thereof do not have a limiting meaning where these terms appear in the description and claims. Accordingly, the terms "comprising", "including", and "having" can be used interchangeably.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are now described. All publications and patents specifically mentioned herein are incorporated by reference for all purposes including describing and disclosing the chemicals, instruments, statistical analysis and methodologies which are reported in the publications which might be used in connection with the invention. All references cited in this specification are to be taken as indicative of the level of skill in the art.

The terminology as set forth herein is for description of the embodiments only and should not be construed as limiting of the invention as a whole. Unless otherwise specified, "a," "an," "the," and "at least one" are used interchangeably and mean one or more than one.

The disclosure is inclusive of the compounds described herein (including intermediates) in any of their pharmaceutically acceptable forms, including isomers (e.g., diastereomers and enantiomers), tautomers, salts, solvates, polymorphs, prodrugs, and the like. In particular, if a compound is optically active, the invention specifically includes each of the compound's enantiomers as well as racemic mixtures of the enantiomers. It should be understood that the term "compound" includes any or all of such forms, whether explicitly stated or not (although at times, "salts" are explicitly stated).

"Pharmaceutically acceptable" as used herein means that the compound or composition or carrier is suitable for administration to a subject to achieve the treatments described herein, without unduly deleterious side effects in light of the necessity of the treatment.

The term "effective amount," as used herein, refers to the amount of the compounds or dosages that will elicit the biological or medical response of a subject, tissue or cell that is being sought by the researcher, veterinarian, medical doctor or other clinician.

As used herein, "pharmaceutically-acceptable carrier" includes any and all dry powder, solvents, dispersion media, coatings, antibacterial and antifungal agents, isotonic agents, absorption delaying agents, and the like. Pharmaceutically-acceptable carriers are materials, useful for the purpose of administering the compounds in the method of the present invention, which are preferably non-toxic, and may be solid, liquid, or gaseous materials, which are otherwise inert and pharmaceutically acceptable, and are compatible with the compounds of the present invention. Examples of such carriers include, without limitation, various lactose, mannitol, oils such as corn oil, buffers such as PBS, saline, polyethylene glycol, glycerin, polypropylene glycol, dimethylsulfoxide, an amide such as dimethylacetamide, a protein such as albumin, and a detergent such as Tween 80, mono- and oligopolysaccharides such as glucose, lactose, cyclodextrins and starch.

The term "administering" or "administration," as used herein, refers to providing the compound or pharmaceutical composition of the invention to a subject suffering from or at risk of the diseases or conditions to be treated or prevented.

A route of administration in pharmacology is the path by which a drug is taken into the body. Routes of administration may be generally classified by the location at which the substance is applied. Common examples may include oral and intravenous administration. Routes can also be classified based on where the target of action is. Action may be topical (local), enteral (system-wide effect, but delivered through the gastrointestinal tract), or parenteral (systemic action, but delivered by routes other than the GI tract), via lung by inhalation.

A topical administration emphasizes local effect, and substance is applied directly where its action is desired. Sometimes, however, the term topical may be defined as applied to a localized area of the body or to the surface of a body part, without necessarily involving target effect of the substance, making the classification rather a variant of the classification based on application location. In an enteral administration, the desired effect is systemic (non-local), substance is given via the digestive tract. In a parenteral administration, the desired effect is systemic, and substance is given by routes other than the digestive tract.

Non-limiting examples for topical administrations may include epicutaneous (application onto the skin), e.g., allergy testing or typical local anesthesia, inhalational, e.g. asthma medications, enema, e.g., contrast media for imaging of the bowel, eye drops (onto the conjunctiva), e.g., antibiotics for conjunctivitis, ear drops, such as antibiotics and corticosteroids for otitis externa, and those through mucous membranes in the body.

Enteral administration may be administration that involves any part of the gastrointestinal tract and has systemic effects. The examples may include those by mouth (orally), many drugs as tablets, capsules, or drops, those by gastric feeding tube, duodenal feeding tube, or gastrostomy, many drugs and enteral nutrition, and those rectally, various drugs in suppository.

Examples of parenteral administrations may include intravenous (into a vein), e.g. many drugs, total parenteral nutrition intra-arterial (into an artery), e.g., vasodilator drugs in the treatment of vasospasm and thrombolytic drugs for treatment of embolism, intraosseous infusion (into the bone marrow), intra-muscular, intracerebral (into the brain parenchyma), intracerebroventricular (into cerebral ventricular system), intrathecal (an injection into the spinal canal), and subcutaneous (under the skin). Among them, intraosseous infusion is, in effect, an indirect intravenous access because the bone marrow drains directly into the venous system. Intraosseous infusion may be occasionally used for drugs and fluids in emergency medicine and pediatrics when intravenous access is difficult.

As used herein, the term "intraperitoneal injection" or "IP injection" refers to the injection of a substance into the peritoneum (body cavity). IP injection is more often applied to animals than to humans. In general, IP injection may be preferred when large amounts of blood replacement fluids are needed, or when low blood pressure or other problems prevent the use of a suitable blood vessel for intravenous injection.

II. The Invention

In certain aspects, the disclosure is directed to alkylphosphocholine analogs labeled with a radioactive metal isotope for detection/imaging of malignant tumor cells in a subject or in a biological sample. The alkylphosphocholine analogs include a chelating moiety that chelates the radioactive metal isotope.

A. Radioactive Metal Isotopes for Malignant Solid Tumor Treatment

For the disclosed methods of therapeutically treating malignant solid tumors, any radioactive metal isotope known to emit ionizing radiation in a form that would result in the death of cells that take up the analogs labeled with the radioactive metal isotope can be incorporated by chelation into the alkylphosphocholine targeting backbone. In some embodiments, the radioactive metal isotope emits its ionizing radiation in a form that minimizes damage to tissue outside of the cells that take up the labeled analogs.

Non-limiting examples of radioactive metal isotopes that could be used include Lu-177, Y-90, Ho-166, Re-186, Re-188, Cu-67, Au-199, Rh-105, Ra-223, Ac-225, As-211, Pb-212, or Th-227.

B. Radioactive Metal Isotopes for Malignant Solid Tumor Detection/Imaging

For the disclosed methods of detecting/imaging malignant solid tumors, any radioactive metal isotope known to emit radiation in a form that is readily detectable by conventional imaging means can be incorporated into the targeting backbone. Non-limiting examples of "conventional imaging means" include gamma ray detection, PET scanning, and SPECT scanning. Non-limiting examples of radioactive metal isotopes that could be used include Ga-66, Cu-64, Y-86, Co-55, Zr-89, Sr-83, Mn-52, As-72, Sc-44, Ga-67, In-111, or Tc-99m.

C. Metal Chelates of PLE Analogs

The disclosed structures utilize an alkylphosphocholine carrier backbone. Once synthesized, the agents must harbor formulation properties that render them suitable for injection while retaining tumor selectivity. A non-limiting exemplary series of metal chelate-PLE analogs follows (additional non-limiting examples were described previously). The structures shown include a chelating moiety to which the radioactive metal isotope is chelated to produce the final imaging or therapeutic agent.

23     24
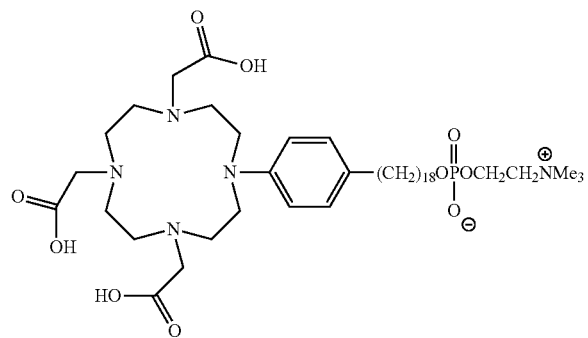
1
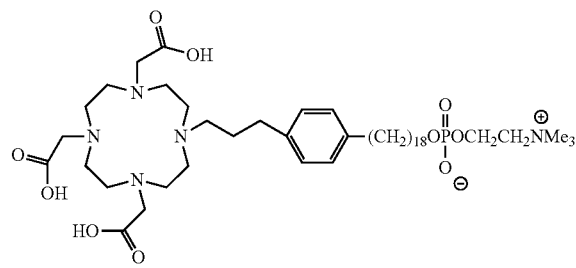
2
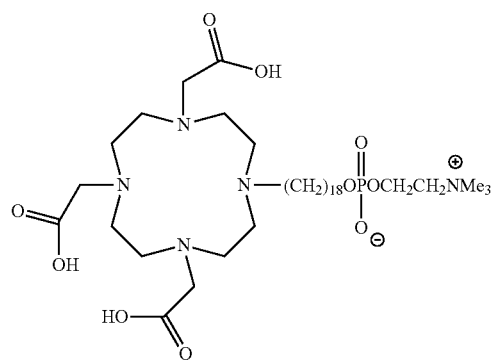
3
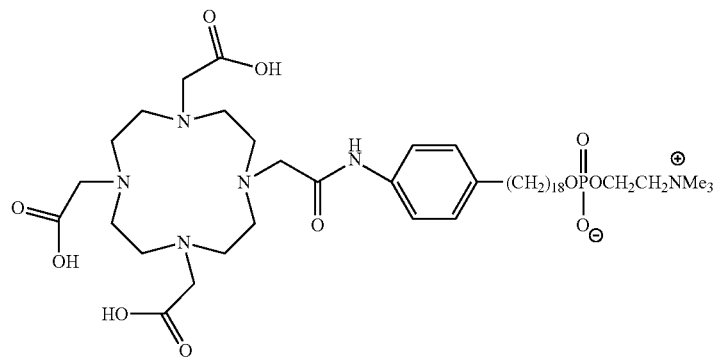
4
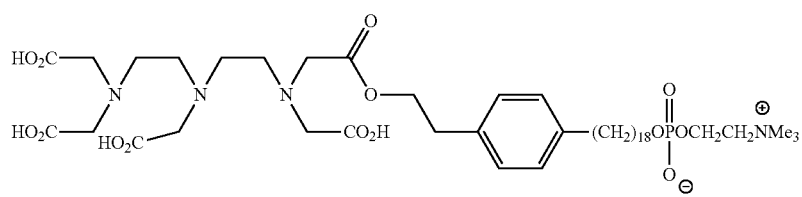
5
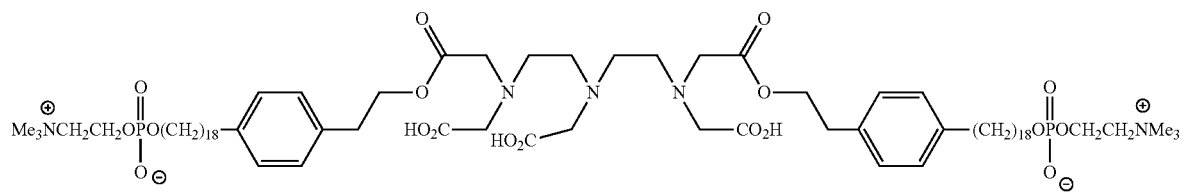
6

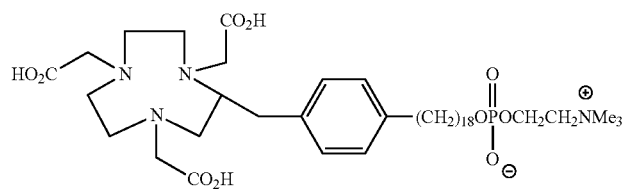

D. Methods of Synthesizing Exemplary M-PLE Analogs

Proposed synthesis of compound 1 is shown below. The first step of the synthesis is similar to described in *Org Synth*, 2008, 85, 10-14. The synthesis is started from cyclen which is converted into DO3A tris-Bn ester. This intermediate is then conjugated with NM404 in the presence of the base and Pd catalyst. Finally, benzyl protecting groups are removed by the catalytic hydrogenation.

Synthesis of compound 2 is shown below. It begins with DO3A tris-Bn ester which is alkylated with 3-(bromo-prop-1-ynyl)-trimethylsilane. After alkylation, the trimethjylsilyl group is removed and the intermediate acetylene is coupled with NM404 by the Sonogashira reaction. The benzyl groups are removed and the triple bond is hydrogenated simultaneously in the last step of the synthesis.

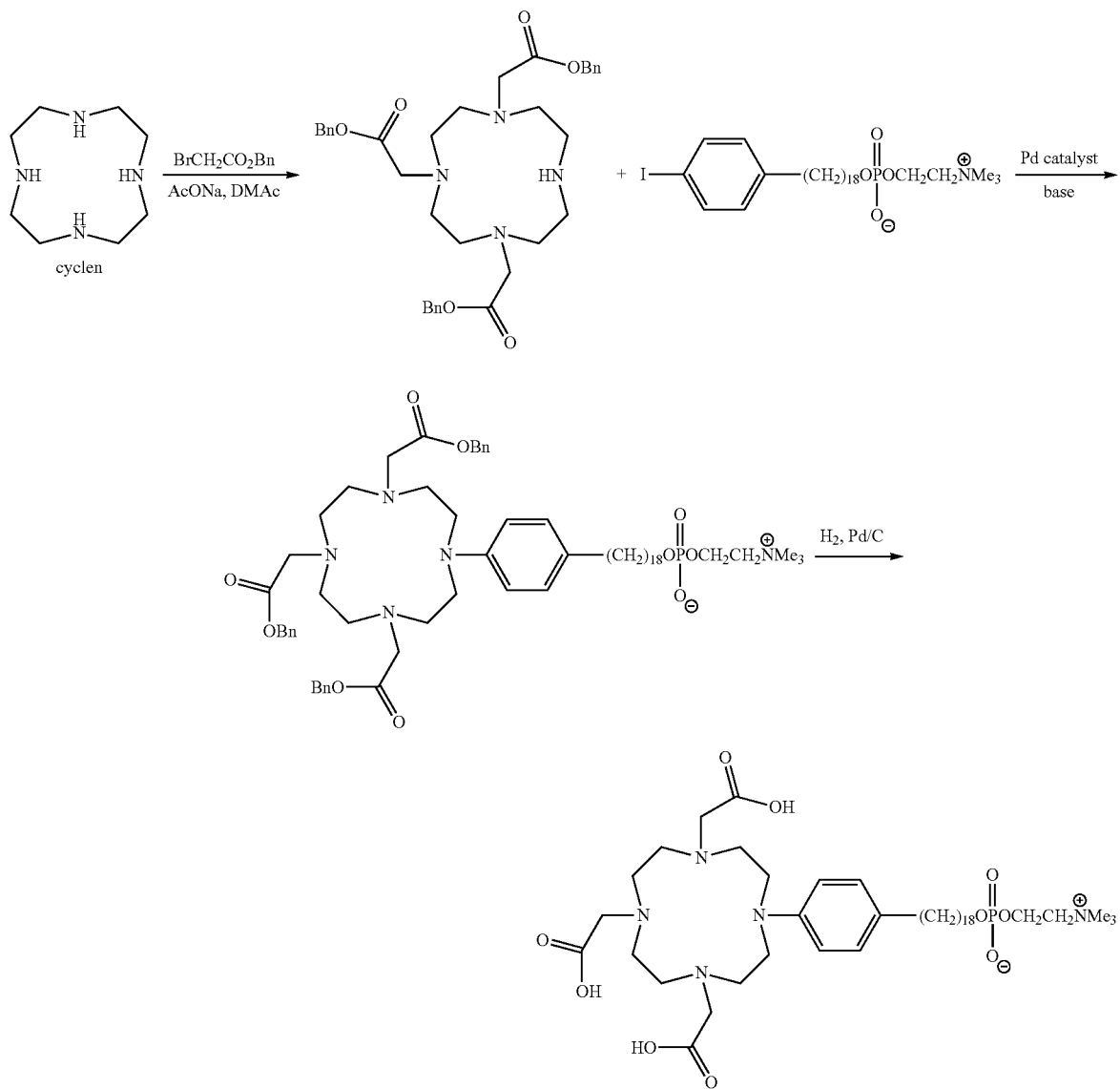

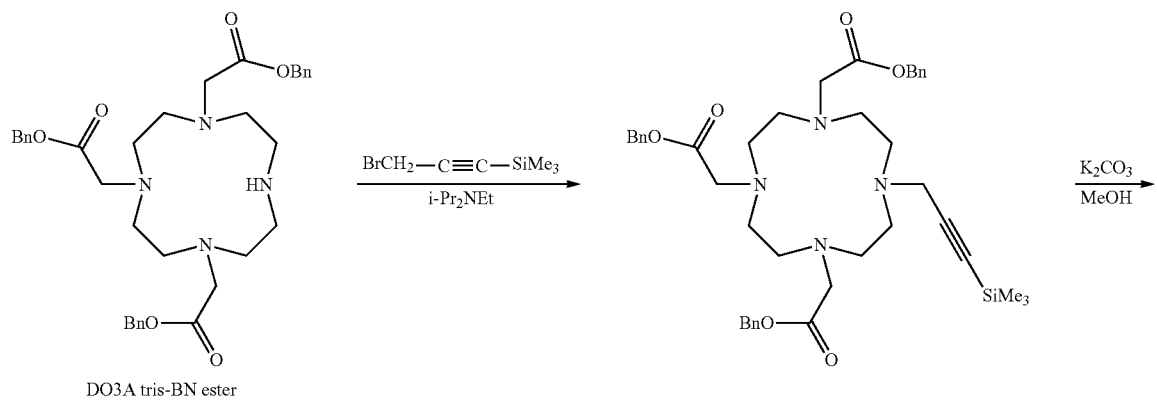
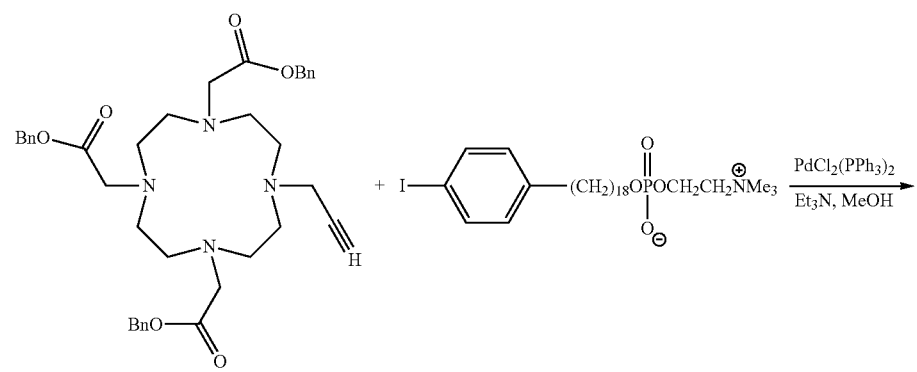
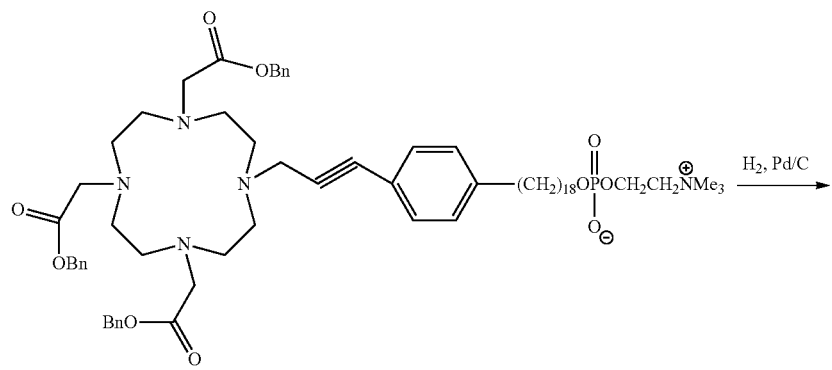
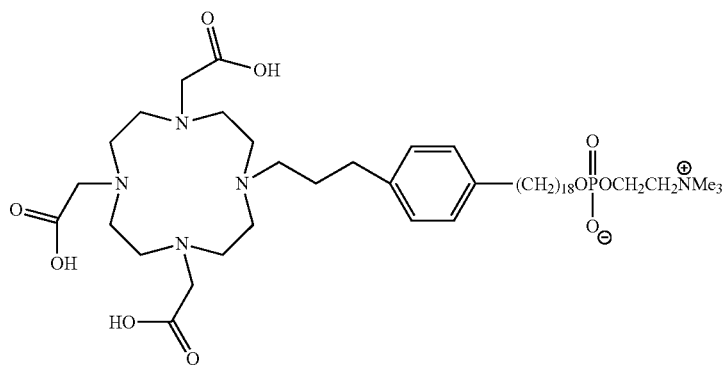

Compounds 5 and 6 can be synthesized from same precursors, DTPA dianhydride and 18-p-(3-hydroxyethyl-phenyl)-octadecyl phosphocholine as shown in the schemes below.

alkylphosphocholine analogs may be administered to the subject via any other suitable systemic deliveries, such as parenteral, intranasal, sublingual, rectal, or transdermal administrations.

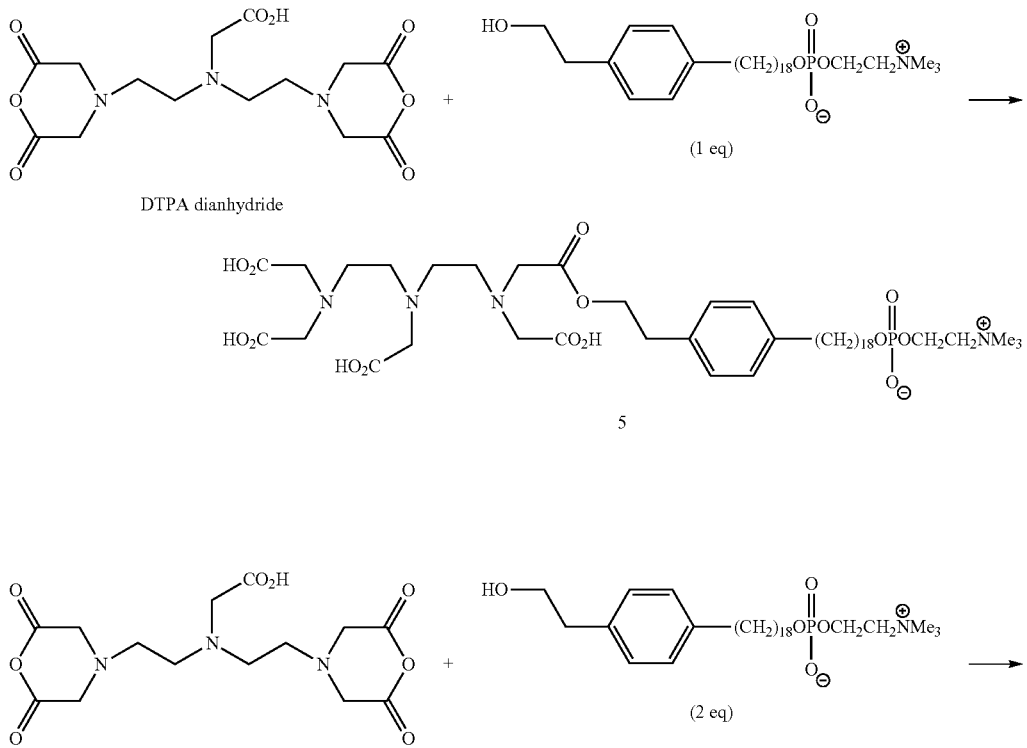

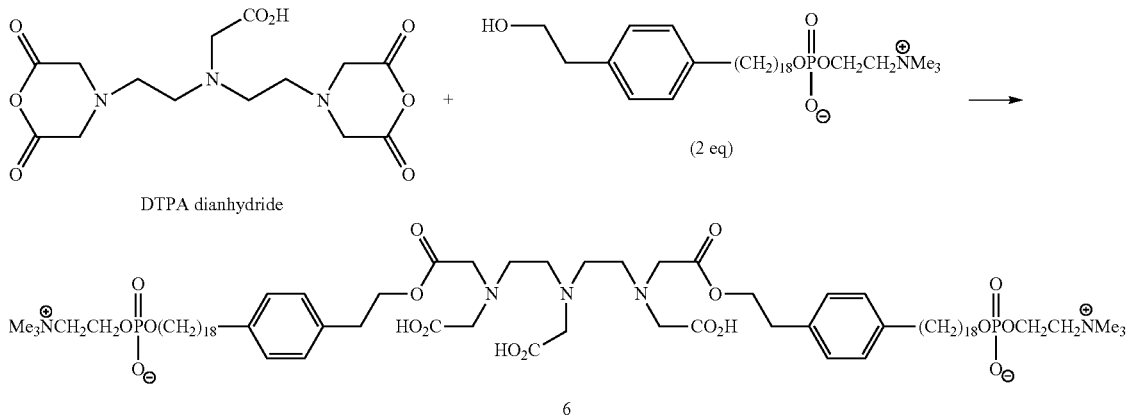

NOTA-NM404 conjugates can be synthesized in an analogous manner. One example of NOTA-NM404 conjugate 7:

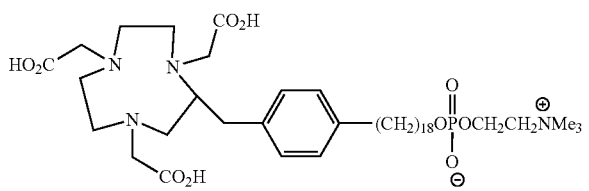

E. Dosage Forms and Administration Methods

Any route of administration may be suitable for administering the disclosed alkylphosphocholine analogs to a subject. In one embodiment, the disclosed alkylphosphocholine analogs may be administered to the subject via intravenous injection. In another embodiment, the disclosed In another embodiment, the disclosed alkylphosphocholine analogs may be administered to the subject via nasal systems or mouth through, e.g., inhalation.

In another embodiment, the disclosed alkylphosphocholine analogs may be administered to the subject via intraperitoneal injection or IP injection.

In certain embodiments, the disclosed alkylphosphocholine analogs may be provided as pharmaceutically acceptable salts. Other salts may, however, be useful in the preparation of the alkylphosphocholine analogs or of their pharmaceutically acceptable salts. Suitable pharmaceutically acceptable salts include, without limitation, acid addition salts which may, for example, be formed by mixing a solution of the alkylphosphocholine analog with a solution of a pharmaceutically acceptable acid such as hydrochloric acid, sulphuric acid, methanesulphonic acid, fumaric acid, maleic acid, succinic acid, acetic acid, benzoic acid, oxalic acid, citric acid, tartaric acid, carbonic acid or phosphoric acid.

Where the disclosed alkylphosphocholine analogs have at least one asymmetric center, they may accordingly exist as enantiomers. Where the disclosed alkylphosphocholine analogs possess two or more asymmetric centers, they may additionally exist as diastereoisomers. It is to be understood that all such isomers and mixtures thereof in any proportion are encompassed within the scope of the present disclosure.

The disclosure also includes methods of using pharmaceutical compositions comprising one or more of the disclosed alkylphosphocholine analogs in association with a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, auto-injector devices or suppositories; for parenteral, intranasal, sublingual or rectal administration, or for administration by inhalation or insufflation.

For preparing solid compositions such as tablets, the principal active ingredient is mixed with a pharmaceutically acceptable carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture for a compound of the present invention, or a pharmaceutically acceptable salt thereof. When referring to these preformulation compositions as homogeneous, it is meant that the active ingredient is dispersed evenly throughout the composition so that the composition may be easily subdivided into equally effective unit dosage forms such as tablets, pills and capsules. This solid pre-formulation composition is then subdivided into unit dosage forms of the type described above containing from 0.1 to about 500 mg of the active ingredient of the present invention. Typical unit dosage forms contain from 1 to 100 mg, for example, 1, 2, 5, 10, 25, 50 or 100 mg, of the active ingredient. The tablets or pills of the novel composition can be coated or otherwise compounded to provide a dosage affording the advantage of prolonged action. For example, the tablet or pill can comprise an inner dosage and an outer dosage component, the latter being in the form of an envelope over the former. The two components can be separated by an enteric layer which, serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the alkylphosphocholine analogs may be incorporated for administration orally or by injection include aqueous solutions, suitably flavored syrups, aqueous or oil suspensions, and flavored emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium caboxymethylcellulose, methylcellulose, polyvinylpyrrolidone or gelatin.

The disclosed alkylphosphocholine analogs are particularly useful when formulated in the form of a pharmaceutical injectable dosage, including in combination with an injectable carrier system. As used herein, injectable and infusion dosage forms (i.e., parenteral dosage forms) include, but are not limited to, liposomal injectables or a lipid bilayer vesicle having phospholipids that encapsulate an active drug substance. Injection includes a sterile preparation intended for parenteral use.

Five distinct classes of injections exist as defined by the USP: emulsions, lipids, powders, solutions and suspensions. Emulsion injection includes an emulsion comprising a sterile, pyrogen-free preparation intended to be administered parenterally. Lipid complex and powder for solution injection are sterile preparations intended for reconstitution to form a solution for parenteral use. Powder for suspension injection is a sterile preparation intended for reconstitution to form a suspension for parenteral use. Powder lyophilized for liposomal suspension injection is a sterile freeze dried preparation intended for reconstitution for parenteral use that is formulated in a manner allowing incorporation of liposomes, such as a lipid bilayer vesicle having phospholipids used to encapsulate an active drug substance within a lipid bilayer or in an aqueous space, whereby the formulation may be formed upon reconstitution. Powder lyophilized for solution injection is a dosage form intended for the solution prepared by lyophilization ("freeze drying"), whereby the process involves removing water from products in a frozen state at extremely low pressures, and whereby subsequent addition of liquid creates a solution that conforms in all respects to the requirements for injections. Powder lyophilized for suspension injection is a liquid preparation intended for parenteral use that contains solids suspended in a suitable fluid medium, and it conforms in all respects to the requirements for Sterile Suspensions, whereby the medicinal agents intended for the suspension are prepared by lyophilization. Solution injection involves a liquid preparation containing one or more drug substances dissolved in a suitable solvent or mixture of mutually miscible solvents that is suitable for injection.

Solution concentrate injection involves a sterile preparation for parenteral use that, upon addition of suitable solvents, yields a solution conforming in all respects to the requirements for injections. Suspension injection involves a liquid preparation (suitable for injection) containing solid particles dispersed throughout a liquid phase, whereby the particles are insoluble, and whereby an oil phase is dispersed throughout an aqueous phase or vice-versa. Suspension liposomal injection is a liquid preparation (suitable for injection) having an oil phase dispersed throughout an aqueous phase in such a manner that liposomes (a lipid bilayer vesicle usually containing phospholipids used to encapsulate an active drug substance either within a lipid bilayer or in an aqueous space) are formed. Suspension sonicated injection is a liquid preparation (suitable for injection) containing solid particles dispersed throughout a liquid phase, whereby the particles are insoluble. In addition, the product may be sonicated as a gas is bubbled through the suspension resulting in the formation of microspheres by the solid particles.

The parenteral carrier system includes one or more pharmaceutically suitable excipients, such as solvents and co-solvents, solubilizing agents, wetting agents, suspending agents, thickening agents, emulsifying agents, chelating agents, buffers, pH adjusters, antioxidants, reducing agents, antimicrobial preservatives, bulking agents, protectants, tonicity adjusters, and special additives.

The following examples are offered for illustrative purposes only, and are not intended to limit the scope of the present invention in any way. Indeed, various modifications of the invention in addition to those shown and described herein will become apparent to those skilled in the art from the foregoing description and the following examples and fall within the scope of the appended claims.

III. Examples Summary:

In Example 1, we provide an exemplary synthesis that also finds use for the synthesis of analogous compounds chelating radioactive metal isotopes.

In Example 2, we demonstrate that an analog having a chelating agent and chelated metal substituted for the iodine moiety of NM404 (Gd-DO3A-404) is taken up by (and can be imaged in) solid tumor tissue, thus providing proof of concept for using the disclosed metal chelates as TRT and/or imaging agents.

In Example 3, we extended the results of Example 2 to demonstrate the tumor-targeting capabilities and uptake dynamics of Gd-DO3A-404 in two different tumor models.

In Example 4, we report in-vivo biodistribution data for Gd-DO3A-404.

In Example 5, we demonstrate that the tumor-targeting properties of Gd-DO3A-404 reside in the NM404 targeting moiety. Specifically, we compare the tumor uptake and retention data for Gd-DO3A-404 with the same data obtained using DOTA-chelated $Gd^{3+}$ (DOTAREM®).

In Example 6, we demonstrate Gd-DO3A-404 uptake in an orthotopic glioblastoma model.

In Example 7, we disclose biodistribution data for Gd-DOA-404 after being administered to flank A549 xenograft mice.

In Example 8, we demonstrate Gd-DO3A-404 uptake in a triple-negative breast cancer model.

In Example 9, we demonstrate Gd-DO3A-404 uptake in two orthotopic xenograft models.

In Example 10, we demonstrate simultaneous uptake and imaging (PET and MRI) of the gadolinium chelate Gd-DO3A-404, acting as an MRI contrast agent, and the copper radionuclide Cu-64 chelate 64Cu-DO3A-404, which acts as a PET contrast agent.

Example 1: Synthesis of Metal Chelated DO3A-404

In this Example, we show the synthetic scheme used to synthesize one exemplary phospholipid chelate, Gd-DO3A-404. Analogs incorporating various radioactive isotopes could be synthesized in a similar manner, where the radioactive isotope in questions is substituted for Gd.

Scheme for synthesizing Gd-DO3A-404 (the disclosed radioactive metal isotopes can be readily substituted for Gd):

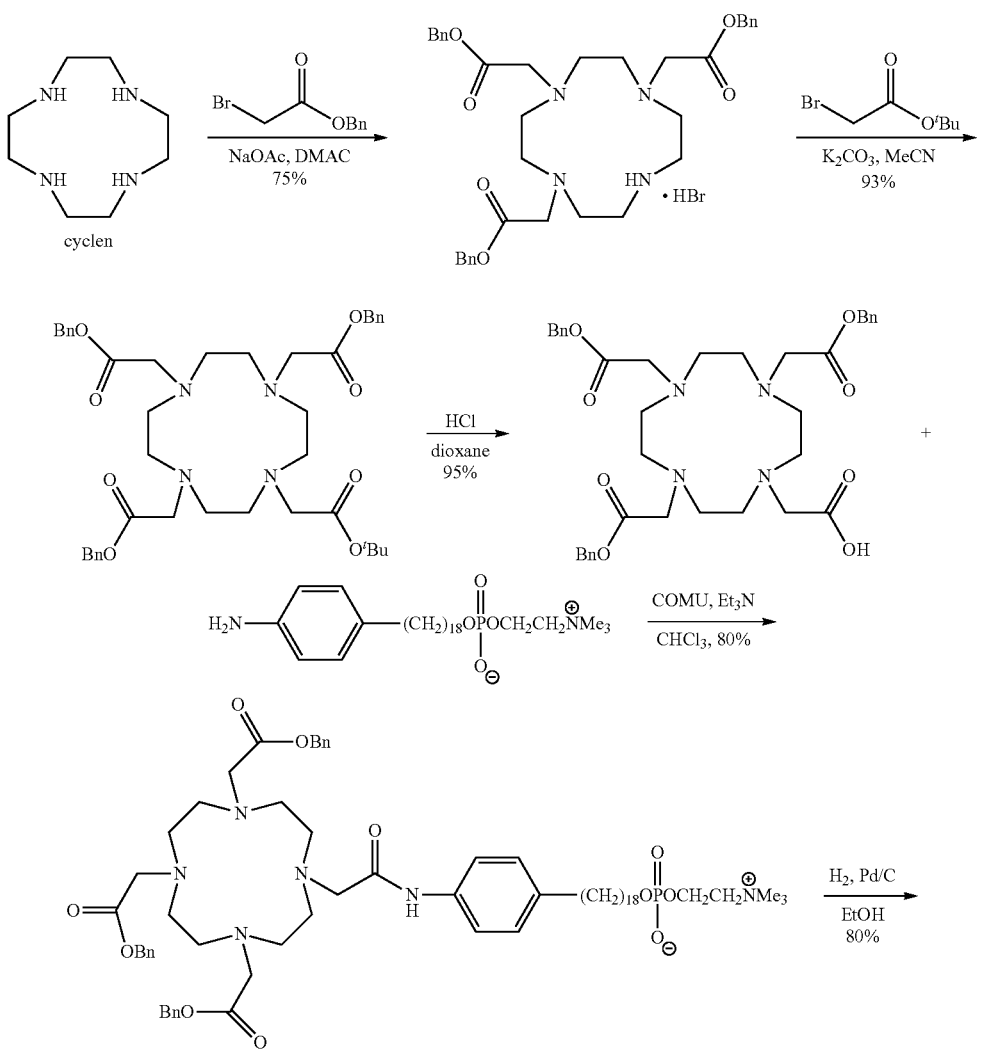

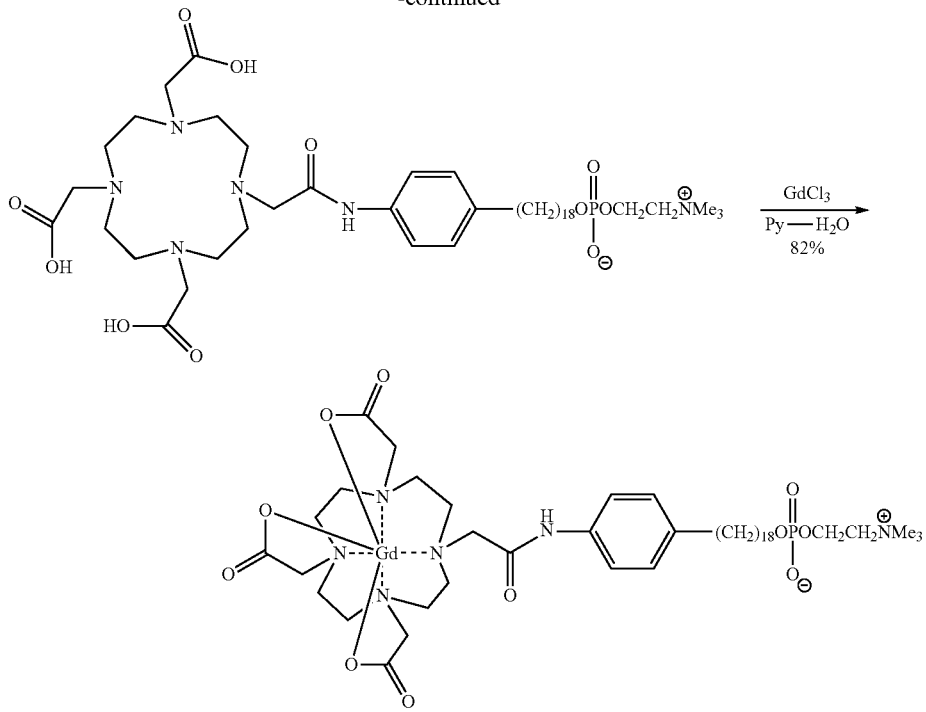

Example 2: In Vivo Imaging Proof of Concept

In this example, we demonstrate the successful in vivo MRI imaging of a tumor, using Gd-DO3A-404 as the MRI contrast agent. The data demonstrates that the backbone phospholipid and chelating agent are taken up and retained by solid tumors, demonstrating that such chelates incorporating various radioactive metals, as disclosed herein, would exhibit similar properties For proof-of-concept in vivo imaging of tumor uptake of the Gd-DO3A-404 agent, nude athymic mouse with a flank A549 tumor (non small cell lung cancer) xenograft was scanned. The Gd-DO3A-404 agent (2.7 mg) was delivered via tail vein injection. Mice were anesthetized and scanning performed prior to contrast administration and at 1, 4, 24, 48, and 72 hours following contrast delivery. Imaging was performed on a 4.7 T Varian preclinical MRI scanner with a volume quadrature coil. T1-weighted images were acquired at all imaging time points using a fast spin echo scan with the following pulse sequence parameters: repetition time (TR)=206 ms, echo spacing=9 ms, echo train length=2, effective echo time (TE)=9 ms, 10 averages, with a 40×40 mm$^2$ field of view, 192×192 matrix, 10 slices of thickness 1 mm each.

Figure 2:
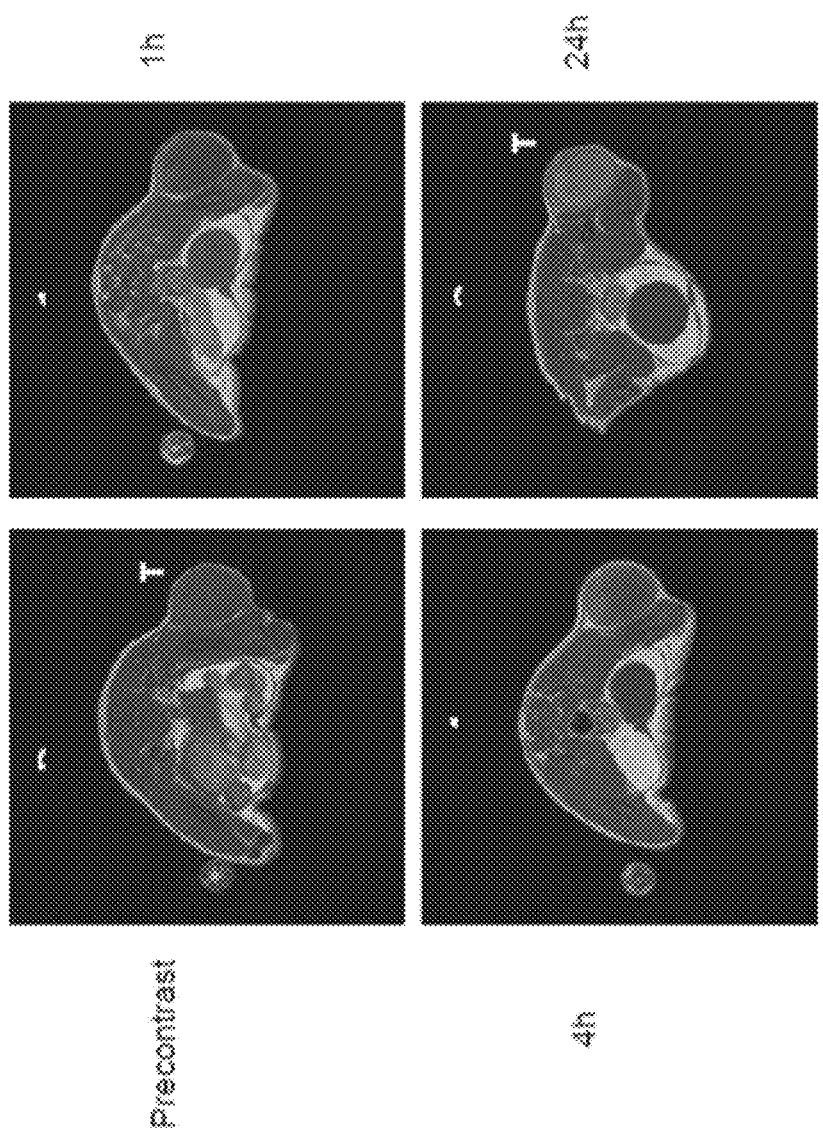
FIG. 2 shows a time course MRI image of a tumor-bearing mouse following injection of Gd-DO3A-404 showing enhancement of the tumor (T) by 24 hours.

As seen in FIG. 2, MRI imaging of the tumor was significantly enhanced by 24 hours post-injection.

These results demonstrate that the differential uptake and retention of alkylphosphocholine analogs is maintained for the metal chelated analogs disclosed herein. Thus, the disclosed metal chelates can readily be applied to clinical therapeutic and imaging applications.

Example 3: In Vivo Cancer Imaging in Multiple Tumor Models

In this extension of Example 2, we demonstrate selective uptake and in vivo MRI imaging in two distinct flank tumor types, using Gd-DO3A-404 as the MRI contrast agent.

To test uptake and retention in rodent models of human cancer, flank xenografts were established in mice for two distinct tumor types, A549 (human non small cell lung cancer, NSCLC) and U87 (human glioma). N=3 for each model. For pre-contrast imaging, $T_1$-W images of the tumor and abdomen (FIG. 4; 2 leftmost images) and $T_1$ maps of the tumor were obtained.

At time zero ("contrast"), 2.5 mg of Gd-DO3A-404 (~12 mmol/kg body mass) was delivered into the mice by intravenous injection. Animals were scanned pre-contrast and at various time points between one hour and seven days post-contrast (after one hour, 24 hours, 48 hours, three days, four days and seven days). $T_1$ maps of the tumor were acquired for each time point, along with $T_1$-weighted images of the tumor and the abdomen (see FIGS. 3 and 4).

Figure 3:
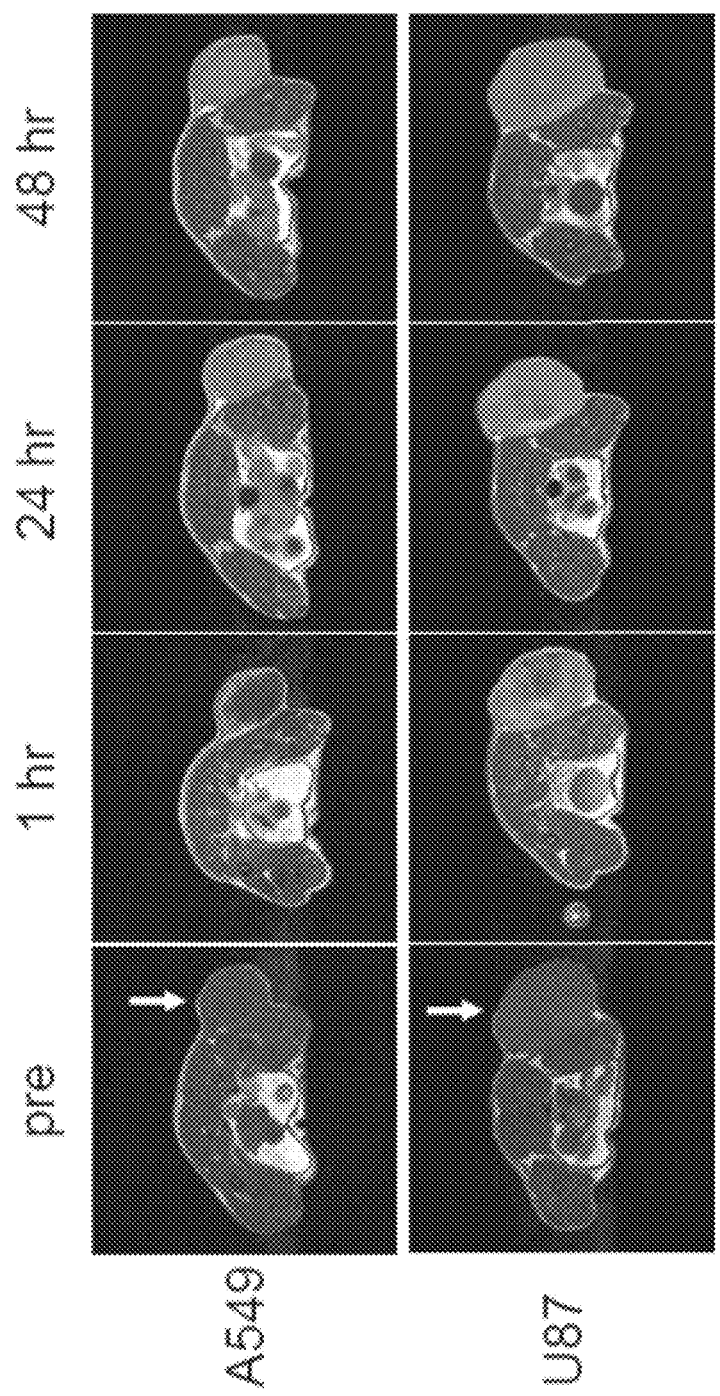
FIG. 3 shows time course MRI images of tumor-bearing mice. The top panel includes images of a mouse bearing a flank A549 (human NSCLC) tumor before contrast agent injection (left, arrow showing tumor location), one hour after injection of Gd-DO3A-404 (second from left), 24 hours following injection of Gd-DO3A-404 (third from left), and 48 hours following injection of Gd-DO3A-404 (rightmost image). The bottom panel includes images of a mouse bearing a flank U87 (human glioma) tumor before contrast agent injection (leftmost image, arrow showing tumor location), one hour after injection of Gd-DO3A-404 (second from left), 24 hours following injection of Gd-DO3A-404 (third from left), and 48 hours following injection of Gd-DO3A-404 (rightmost image).
Figure 4:
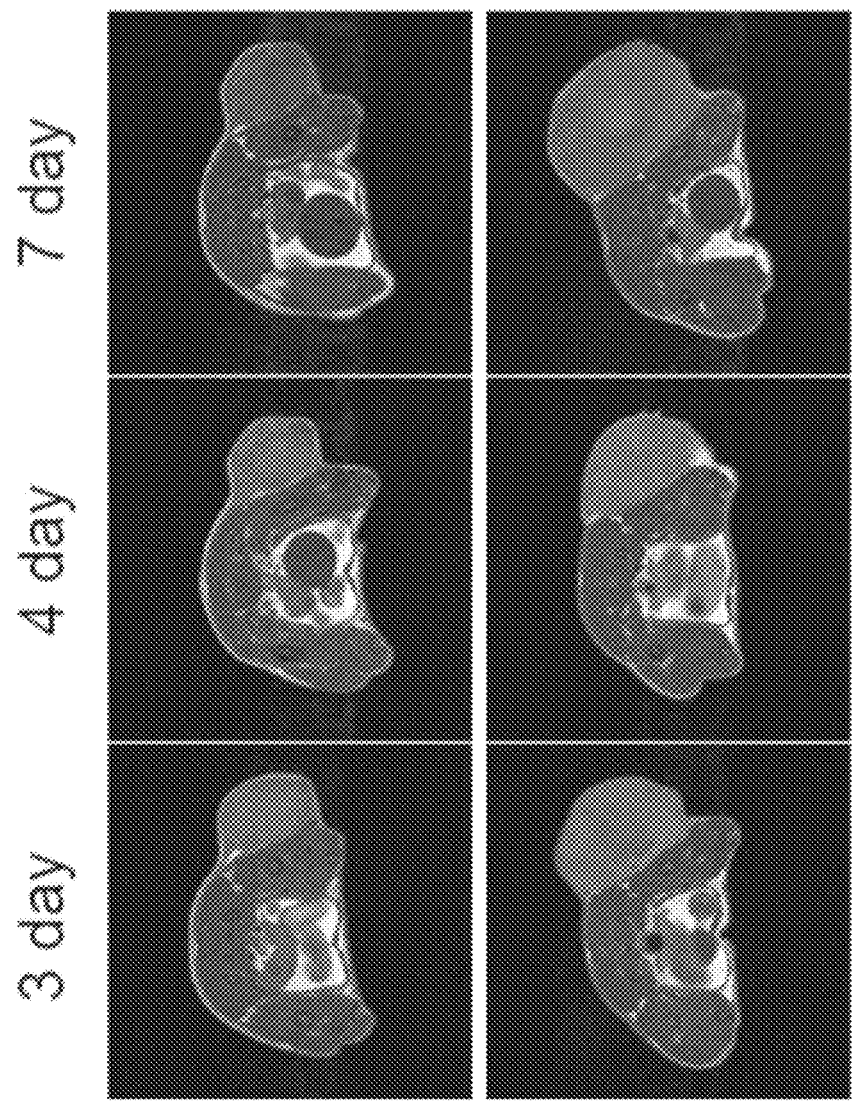
FIG. 4 shows further time course MRI images of tumor-bearing mice, continuing from FIG. 3. The top panel includes images of the mouse bearing a flank A549 (human NSCLC) tumor three days after injection of Gd-DO3A-404 (leftmost image), four days following injection of Gd-DO3A-404 (second from left), and seven days following injection of Gd-DO3A-404 (rightmost image). The bottom panel includes images of the mouse bearing a flank U87 (human glioma) tumor three days after injection of Gd-DO3A-404 (leftmost image), four days following injection of Gd-DO3A-404 (second from left), and seven days following injection of Gd-DO3A-404 (rightmost image).

In the NSCLC model, Gd-DO3A-404 uptake was not immediate and reached a maximum at 24-48 hours post-contrast (FIG. 3). The uptake was maintained over several days (FIG. 4). In the U87 model, uptake was more rapid (already observable at one hour after delivery; see FIG. 3) and appeared to reach higher levels and was maintained for a longer time period (see FIG. 4).

Figure 5:
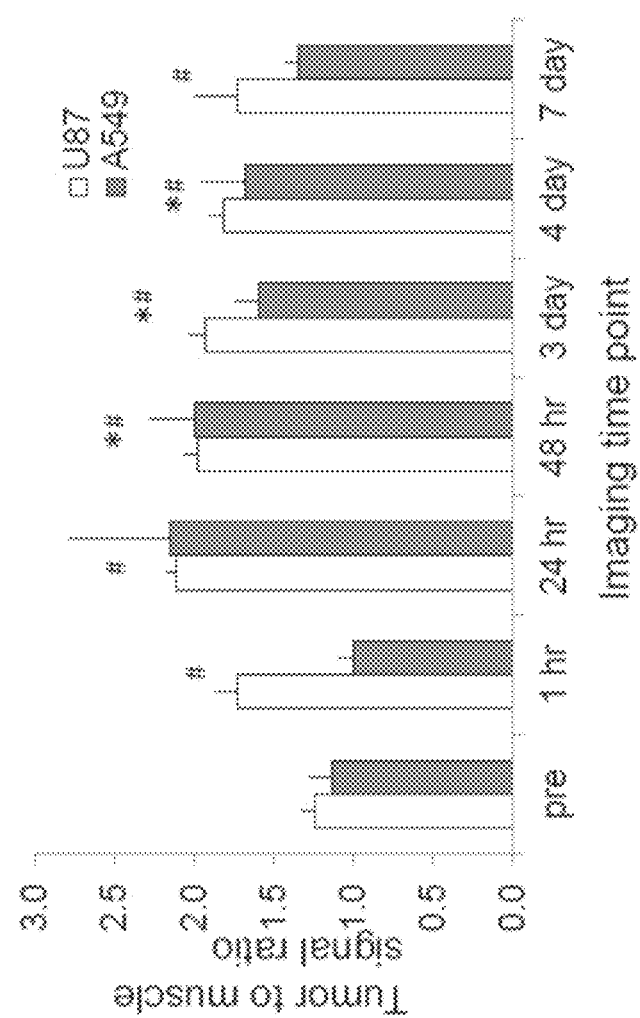
FIG. 5 is a bar graph of quantified results from the images shown in FIGS. 3 and 4. Specifically, the tumor to muscle T1-weighted signal ratios are shown for both the mouse bearing a flank A549 (human NSCLC) tumor (shaded bar) and the mouse bearing a flank U87 (human glioma) tumor (unshaded bar) before contrast agent injection (pre), one hour after injection of Gd-DO3A-404, 24 hours after injection of Gd-DO3A-404, 48 hours after injection of Gd-DO3A-404, three days after injection of Gd-DO3A-404, four days after injection of Gd-DO3A-404, and seven days after injection of Gd-DO3A-404. *$p<0.05$ compared to pre-contrast, A549. #$p<0.05$ compared to pre-contrast, U87.
Figure 6:
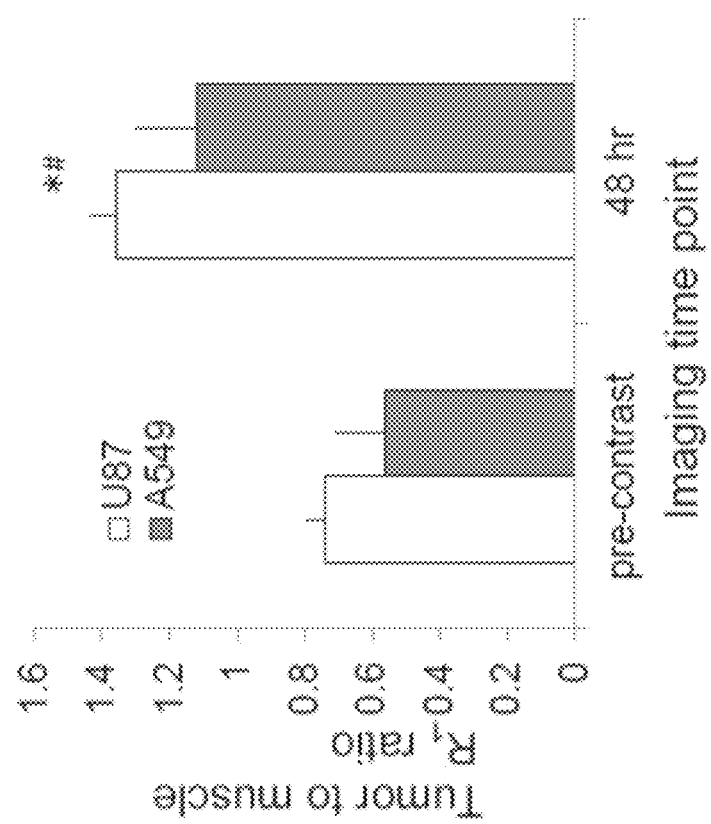
FIG. 6 is a bar graph of quantified results from the images shown in FIGS. 3 and 4. Specifically, the tumor to muscle $R_1$ ratios are shown for both the mouse bearing a flank A549 (human NSCLC) tumor (shaded bar) and the mouse bearing a flank U87 (human glioma) tumor (unshaded bar) before contrast agent injection (pre-contrast), and 48 hours after injection of Gd-DO3A-404. *p<0.05 compared to pre-contrast, A549. # p<0.05 compared to pre-contrast, U87.
Figure 7:
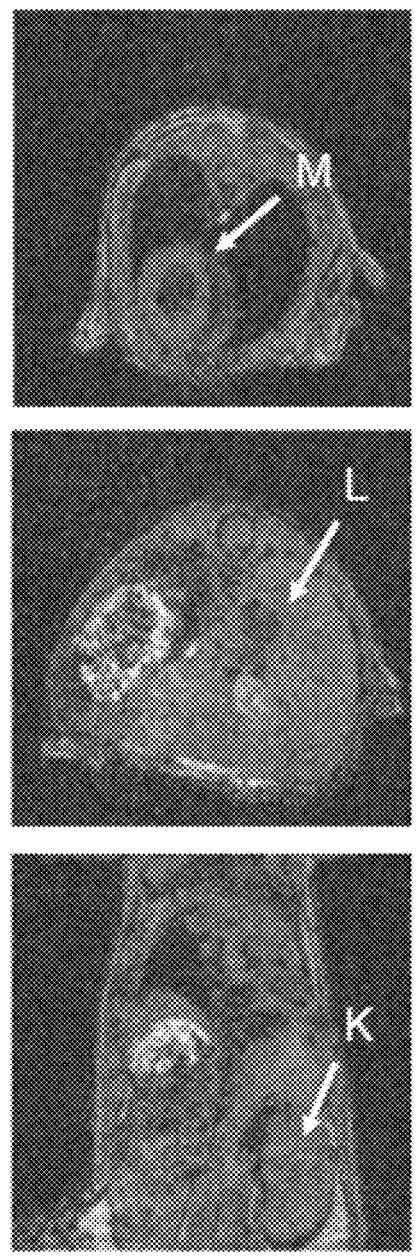
FIGS. 7, 8, 9, 10, and 11 are T1-weighted spoiled gradient (SPGR) magnetic resonance (MR) images of three different mouse abdomen cross-sections, showing in vivo biodistribution of the Gd-DO3A-404 contrast agent.
Figure 8:
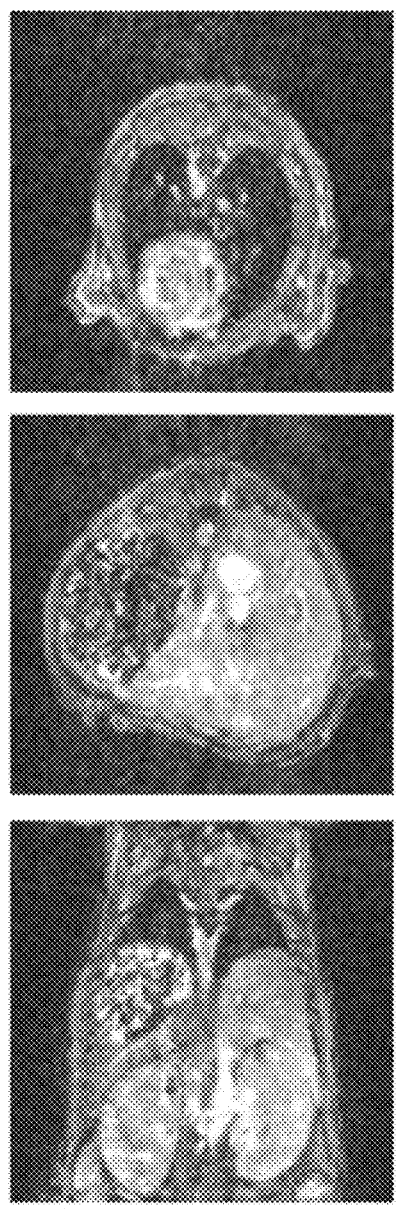
Figure 9:
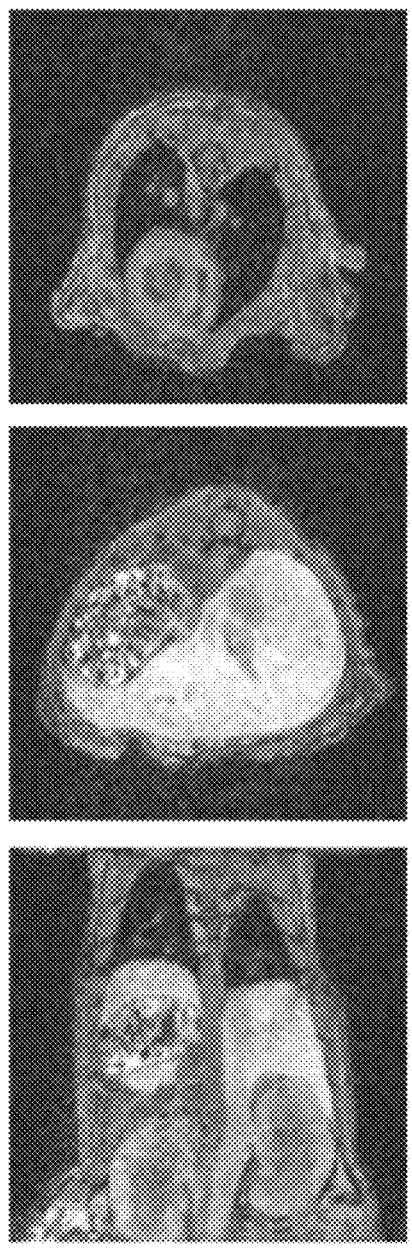
Figure 10:
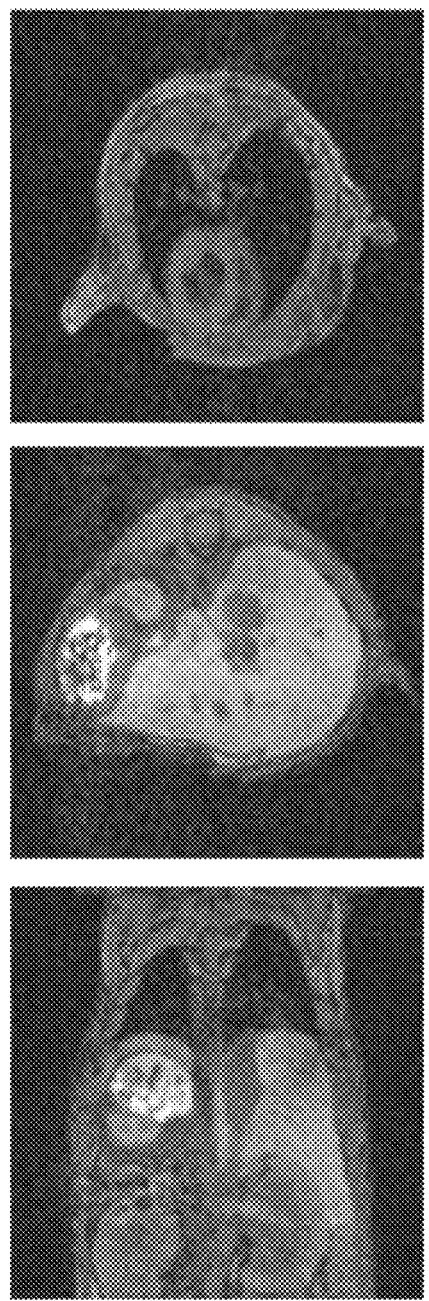

Those observations were confirmed by the quantified data, where tumor to muscle $T_1$-weighted signal ratios were approximately doubled following Gd-DO3A-404 delivery (FIG. 5). The increase in tumor signal was more rapid and more prolonged in U87 tumors as compared to A549 tumors. As seen in FIG. 6, the $R_1$ relaxation rate for both tumor types was significantly increased at 48 hours post-contrast.

In the disclosed metal chelates, a radioactive metal isotope is used instead of gadolinium. However, the rest of the structure, including both the tumor-targeting phospholipid moiety and the chelating agent, read on the disclosed metal chelates. Thus, the results demonstrate that the differential uptake and retention of alkylphosphocholine analogs in multiple tumor types is maintained for the metal chelated analogs disclosed herein. Accordingly, the disclosed metal chelates would be useful in clinical cancer therapeutic and imaging applications.

Example 4: Use of MRI to Determine In Vivo Biodistribution of Gd-DO3A-404

Figure 11:
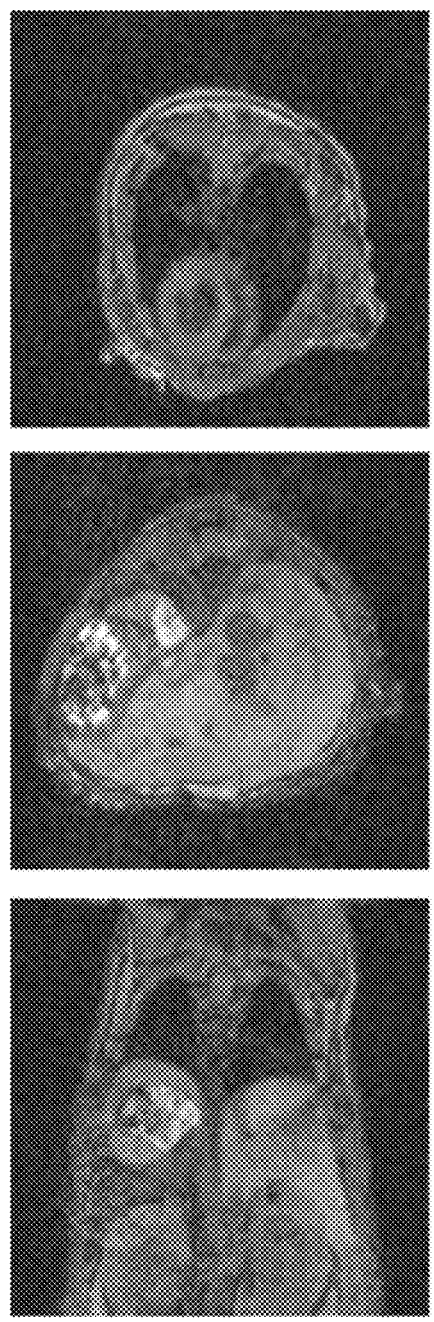

In this Example, we determined the in vivo biodistribution of the Gd-DO3A-404 after the contrast agent was administered (see Example 3). During the course of performing the experiments described in Example 4, we also acquired $T_1$-weighted spoiled gradient (SPGR) images in the abdomen of the mice, to observe biodistribution. Abdominal cross-sections imaged included the myocardium (FIGS. 7-11, top image), the liver (FIGS. 7-11, center image), and a kidney (FIGS. 7-11, bottom image). Images are shown pre-contrast (FIG. 7), and at one hour (FIG. 8), 24 hours (FIG. 9), four days (FIG. 10) and seven days post-contrast (FIG. 11).

In the myocardium and blood pool, the Gd-DO3A-404 contrast agent circulates for nearly up to a day, after which any signal observed is due to retention rather than from further uptake. In the liver and kidney, the Gd-DO3A-404 contrast agent is substantially cleared over time, with more rapid clearance occurring through the liver, and more prolonged clearance occurring through the kidney. Notably, the Gd-DO3A-404 contrast agent exhibits a P-kinetic profile, including hepatobiliary excretion, that is similar to that of related alkylphosphocholine analogs.

Example 5

The Gd-DO3A-404 Targeting Moiety Facilitates Tumor-Selective and Sustained Uptake In this Example, we demonstrate that the selective uptake and retention of Gd-DO3A-404 in tumor tissues is in fact facilitated by the tumor-targeting phospholipid moiety (the "404" moiety; see FIG. 1), rather than by the the gadolinium metal or its chelating agent. Accordingly, this Example demonstrates that effective tumor-targeting agents are not limited to those having a specific chelating agent or metal ion, as long as they include the disclosed tumor-targeting phospholipid moieties.

Figure 12:
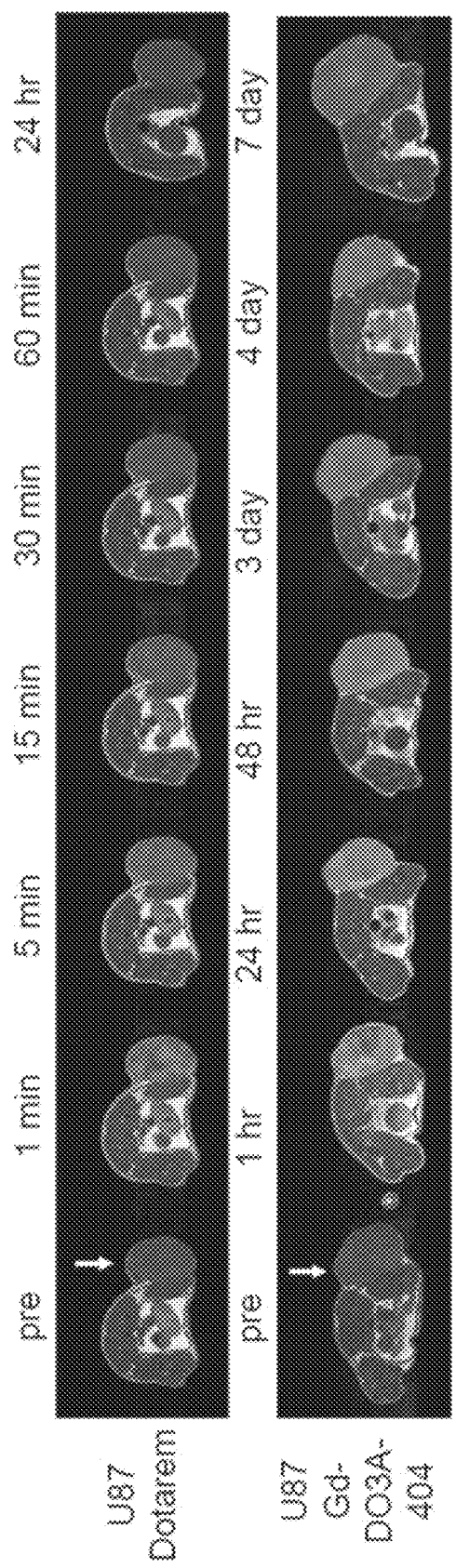
FIG. 12 shows a time course MRI image of tumor-bearing (U87) mice before (pre) and for various times following injection of DOTA-chelated $Gd^{3+}$ (DOTAREM®, top panel) and Gd-DO3A-404 (bottom panel). Tumor location in the mouse flank is indicated by the arrow in the two "pre" images.

To verify that uptake and retention was due to targeting of the "404" moiety, we directly compared the uptake of Gd-DO3A-404 with that of DOTA-chelated $Gd^{3+}$ (DOTA-REM®) in an identical tumor model (mice with flank U87 tumors) and imaging scenario, using the same number of moles of each. As seen in FIG. 12, the uptake and clearance of DOTAREM®, is much more rapid than that of Gd-DO3A-404.

Figure 13:
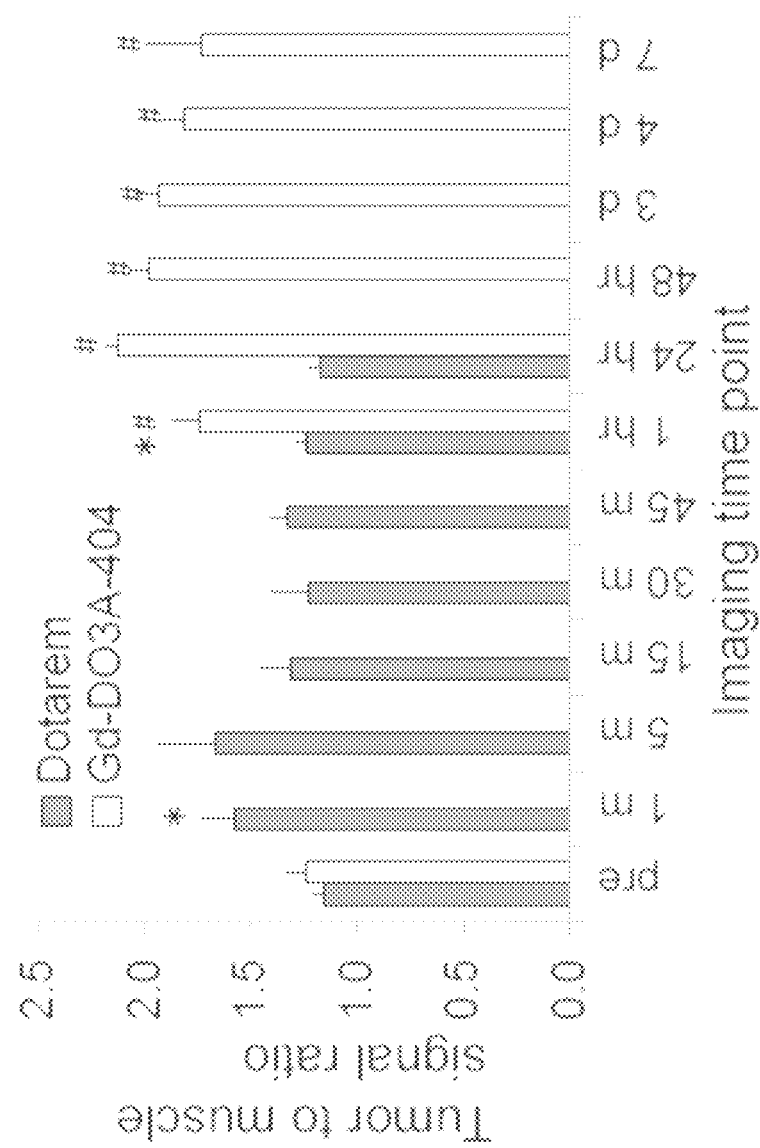
FIG. 13 is a bar graph is a bar graph of quantified results from the images shown in FIG. 13. Specifically, the tumor to muscle signal ratios are shown for both the U87 mouse before (pre) and at various times after injection with DOTAREM® (shaded bars) or Gd-DO3A-404 (unshaded bars). *p<0.05 compared to pre-contrast, DOTAREM®. # p<0.05 compared to pre-contrast, Gd-DO3A-404.

We the quantified the tumor to muscle ratio and compare it to baseline scans. As seen in FIG. 13, the DOTOREM® uptake was less striking, and significant only at a couple of early time points, as compared to Gd-DO3A-404.

These results show that the phospholipid targeting moiety of Gd-DO3A-404 (the 404 moiety), not the chelating agent and chelated metal (the Gd-DO3A moiety) are responsible for the observed selective tumor uptake and retention. Thus, a variety of different chelating moieties and chelated metals can be used without affecting the selective tumor uptake and retention properties of the disclosed chelates.

Example 6: Brain Tumor Uptake of Gd-DO3A-404 in Orthotopic Glioma Model

In this Example, we demonstrate that at higher dosages, Gd-DO3A-404 can pass through the blood-brain barrier to successfully target brain tumor tissue.

To investigate the use of Gd-DO3A-404 to detect tumors and metasteses in situ, in particular, in the brain, we created an orthotopic glioblastoma model using cancer stem cells injected into the brain. To create the model, brains of mice were injected with cells from orthotopic glioblastoma stem cell line 12.6. After sufficient tumor growth, monitored with $T_2$-weighted MRI, we imaged subjects pre-contrast and after delivery (24-72 hours) of two different doses of Gd-DO3A-404 (2.5 or 3.7 mg; ~0.12-0.18 mmole/kg).

Figure 14:
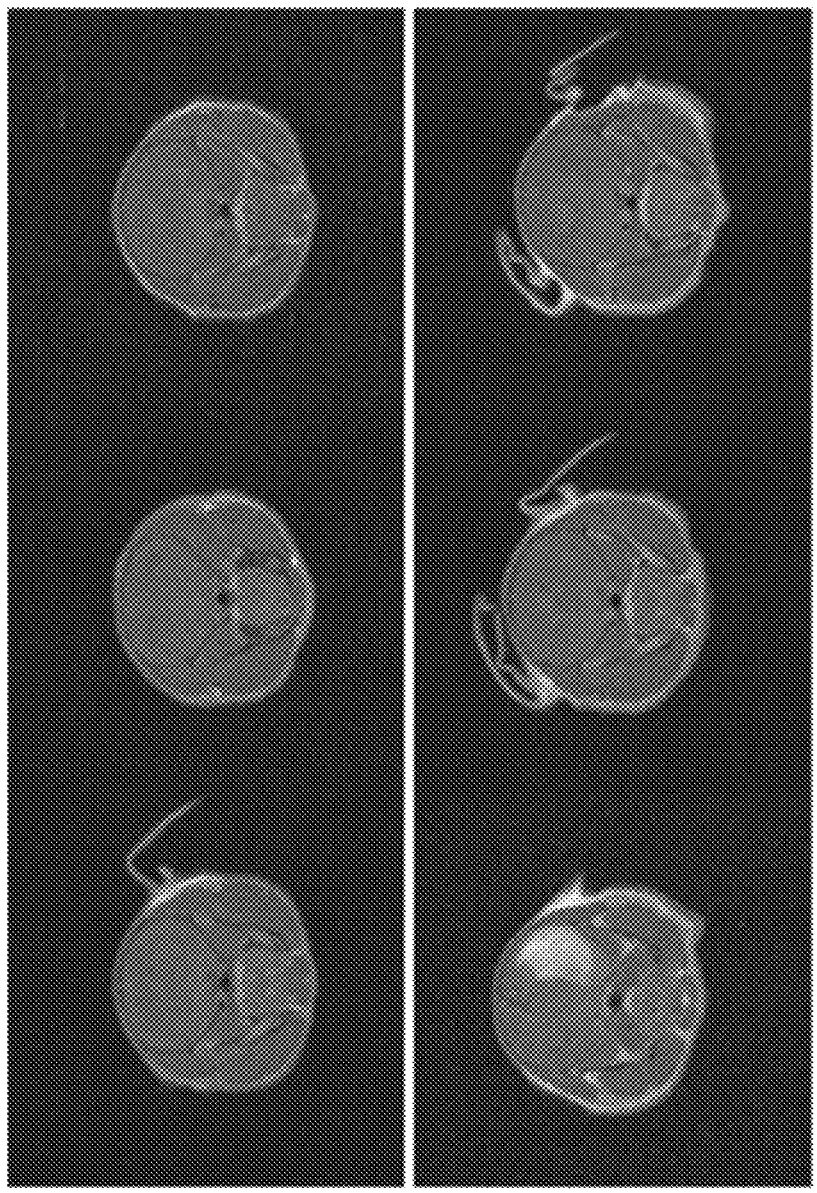
FIG. 14 shows MRI brain images of orthotopic glioblastoma model mice. 2.5 mg (top panel) or 3.7 mg (bottom panel) of Gd-DOA3A-404 was administered to the mice by intravenous injection, and these images were obtained 48 hours after contrast agent injection.

At the lower dose used for flank xenografts, no brain uptake was observed (see FIG. 14, upper panel). Because the lower delivered dose was relatively low (on the same order of that delivered per kg body weight in clinical settings), we increased the dose for another group of animals. In this group, we observed uptake in one subject (FIG. 14, bottom panel). This result indicates that the blood-brain barrier (BBB) may be playing a role in brain tumor uptake, and dosage may be "tuned" to facilitate the contrast agent's passage through the BBB.

Example 7: In Vivo Biodistribution Data for Gd-DO3A-404 in Flank A549 Xenograft Mice In this extension of Example 4, we further examined the in vivo biodistribution of Gd-DO3A-404 after it is administered. Specifically, tissue biodistribution was measured in A549-flank bearing mice 72 hours after administration of Gd-DO3A-404. Nude athymic mice were sacrificed, perfused and tissues were collected and quantitated for Gd by high-resolution (magnetic-sector) inductively-coupled plasma mass spectrometry (SF-ICPMS). n=3 mice.

Figure 15:
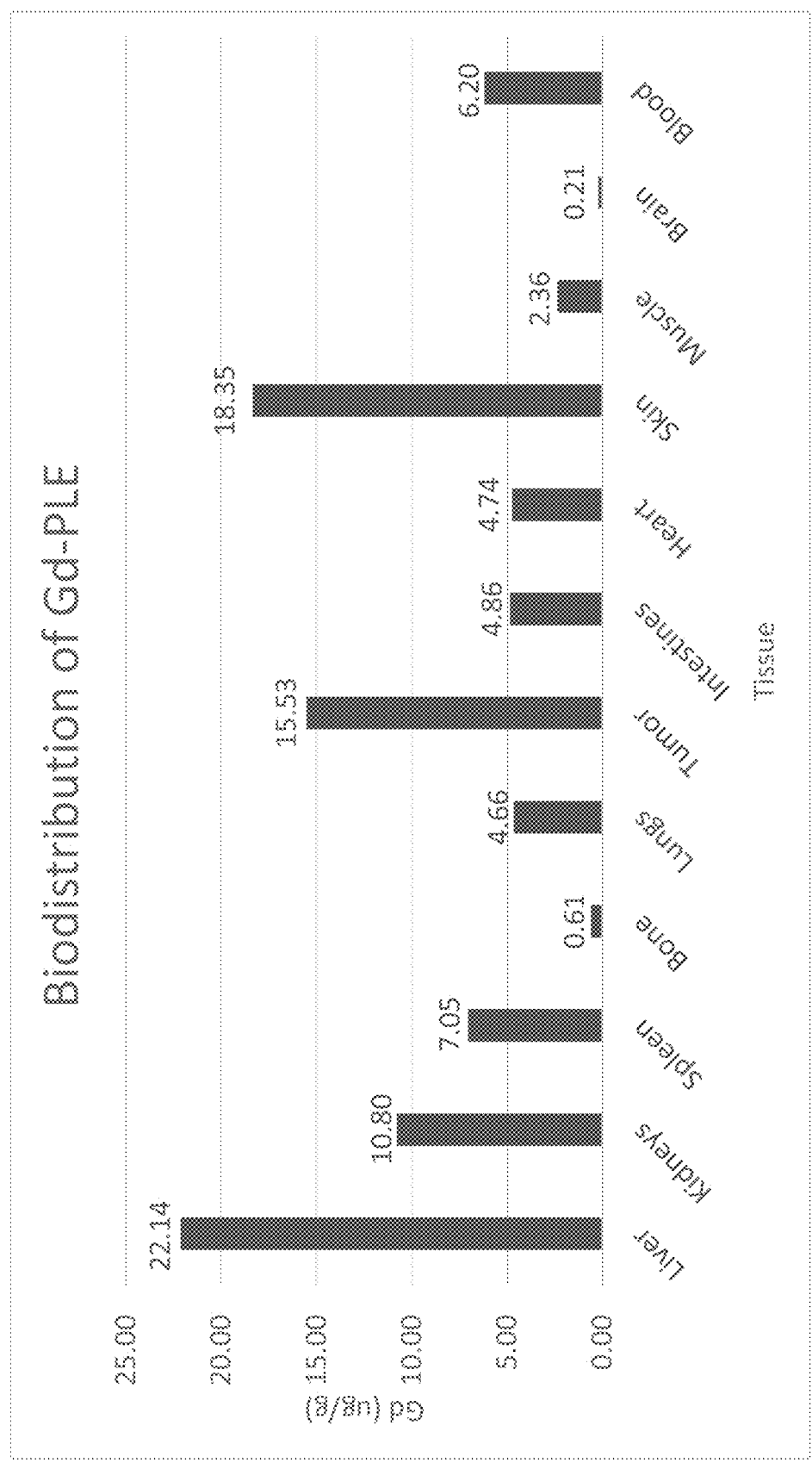
FIG. 15 is a bar graph showing tissue biodistribution of Gd-DO3A-404 in xenograft A549-flank bearing mice 72 hours post-administration. n=3 mice.

As seen in FIG. 15, the Gd-DO3A-404 was selectively taken up by tumor tissue, again demonstrating the suitability of the disclosed alkylphosphocholine analogs for targeted delivery to tumor tissue.

Example 8: Uptake of Gd-DO3A-404 in Triple-Negative Breast Cancer Model

In this example, we demonstrate the successful targeting of Gd-DO3A-404 to breast cancer tissue.

Figure 16:
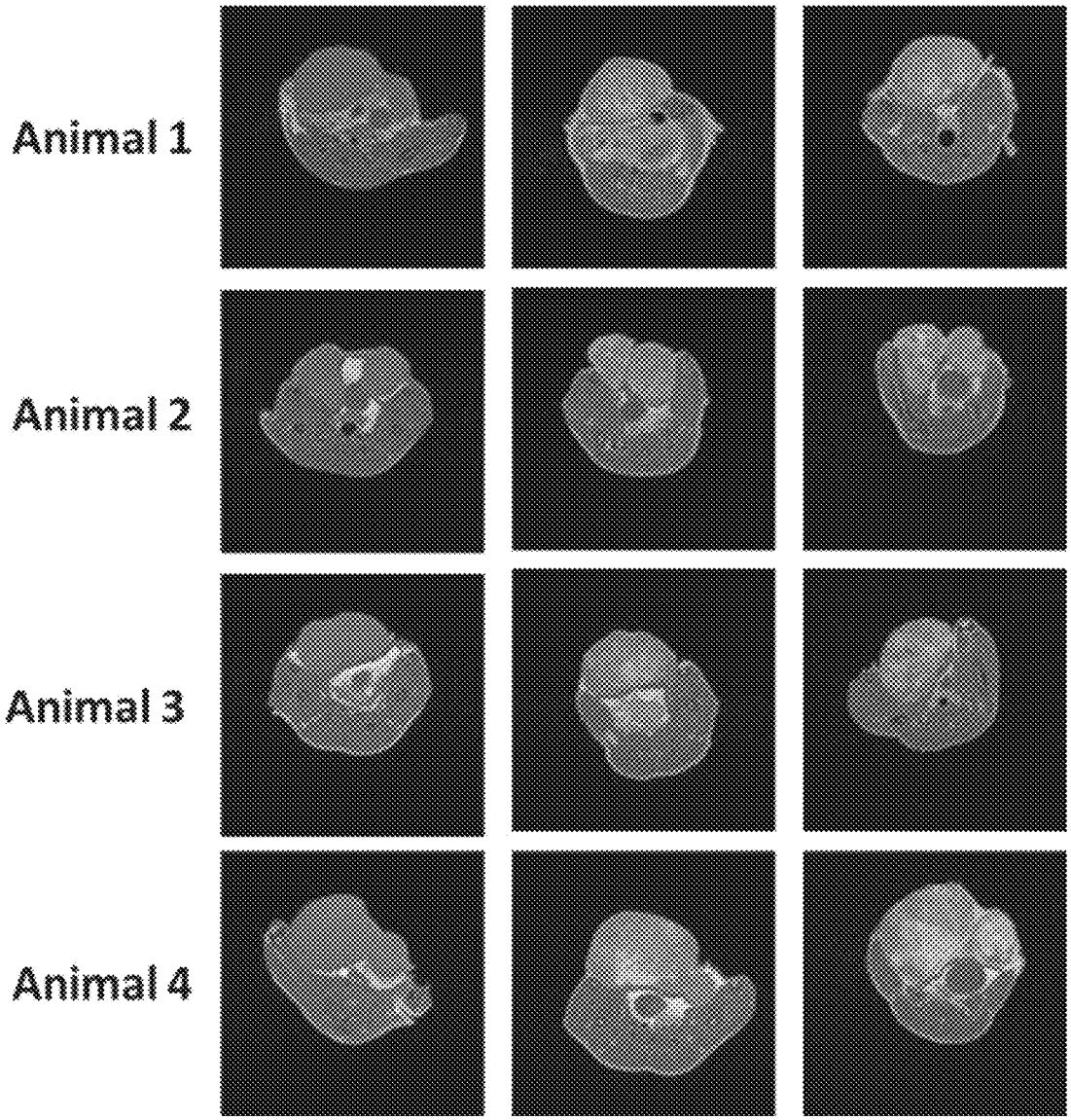
FIG. 16 shows time course MRI images obtained from a transgenic mouse triple-negative breast cancer model (n=4; Animals/rows 1-4). Alpha-beta crystalline overexpressing mice were imaged pre-administration (leftmost column) and 24 hours (center column) and 48 hours (rightmost column) post-administration.

Alpha-beta crystalline overexpressing mice (a triple negative breast cancer model) underwent MR imaging pre administration and 24 hours and 48 hours post-administration of Gd-DO3A-400 (n=4). As seen in FIG. 16, over 48 hours, the contrast agent was taken up by and localized to the breast cancer tissue.

This example illustrates that the disclosed alkylphosphocholine metal chelates can be used to target a wide range of solid tumor tissues.

Example 9: Uptake of Gd-DO3A-404 in Orthotopic Model

In this example, we demonstrate the successful targeting of Gd-DO3A-404 in two different orthotopic xenograft models.

Figure 17:
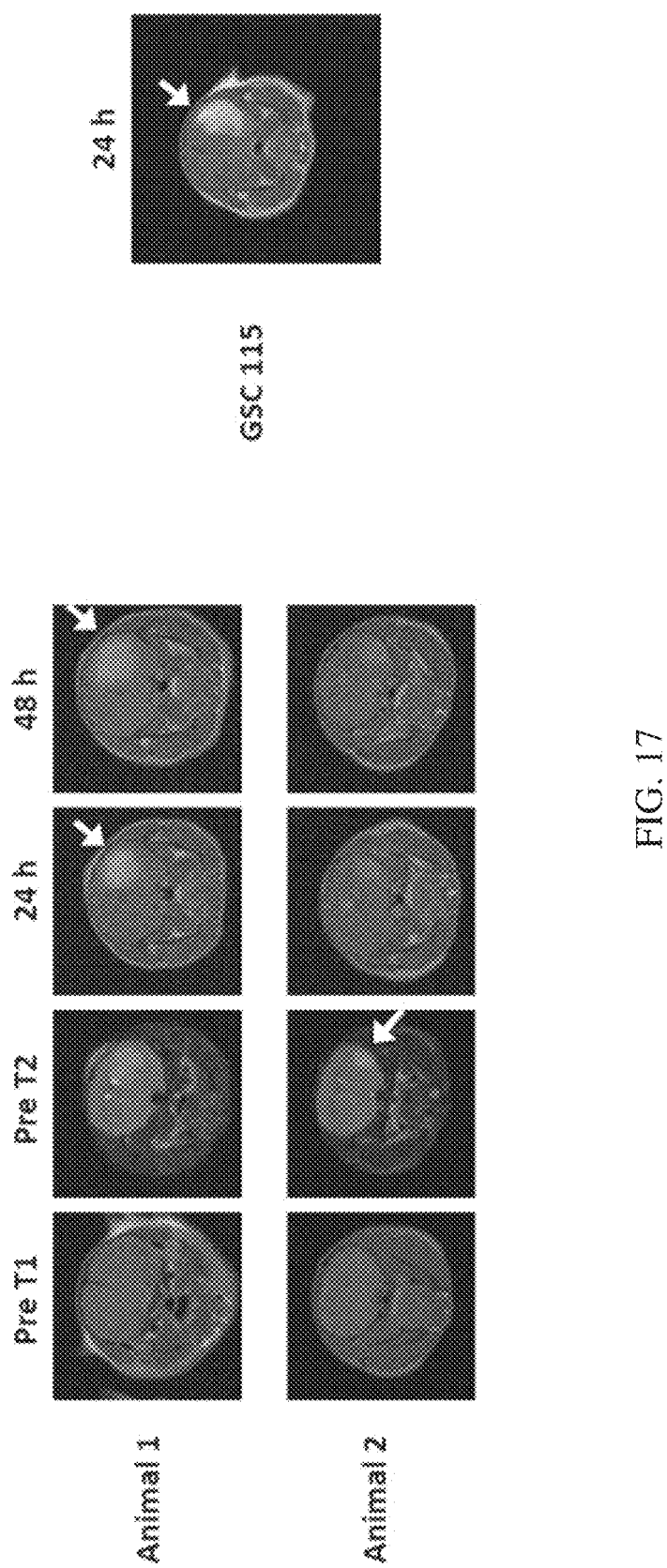
FIG. 17 shows T1-weighted images obtained from orthotopic xenograft mouse models. NOD-SCID mice with orthotopic U87 xenografts were imaged pre-administration, 24 hours, and 48 hours post administration of Gd-DO3A-404 (left panel). Orthotopic GSC 115 was imaged at 24 hours post administration (right panel). GSC is a human glioma stem cell model which was isolated from a human glioma patient.

NOD-SCID mice with orthotopic U87 xenografts were imaged pre-administration, 24 hours, and 48 hours post administration of Gd-DO3A-404. As seen in FIG. 17 (left panel), the contrast agent was differentially taken up by the tumor tissue (see arrows).

Orthotopic GSC 115 was imaged at 24 hours post administration of Gd-DO3A-404. GSC is a human glioma stem cell model which was isolated from a human glioma patient. As seen in FIG. 17 (right panel), the contrast agent was differentially taken up by the tumor tumor tissue (see arrow).

This example illustrates that the disclosed alkylphosphocholine metal chelates can be used to target a wide range of solid tumor tissues.

Example 10: Simultaneous PET/MR Imaging Demonstrating Tumor Targeting by Both Gd-DO3A-404 and $^{64}$Cu-DO3A-404

In this example, we demonstrate the successful use of both Gd-DO3A-404 and $^{64}$Cu-DO3A-404 as tumor targeting contrast agents (Gd-DO3A-404 for MRI and $^{64}$Cu-DO3A-404 for simultaneous PET imaging).

Simultaneous imaging was performed using a clinical Pet/MRI scanner. $^{64}$Cu-DO3A-404 has the same structure as Gd-DO3A-404, except that $^{64}$Cu, a positron emitting radionuclide, is chelated to the chelating moiety instead of Gd. $^{64}$Cu-DO3A-404 was synthesized (and can be synthesized using the methods disclosed herein; see, e.g., Example 1). Both the $^{64}$Cu-DO3A-404 and Gd-DO3A-404 chelates were injected simultaneously into a rat with a flank U87 (human glioma) xenograft.

Figure 18:
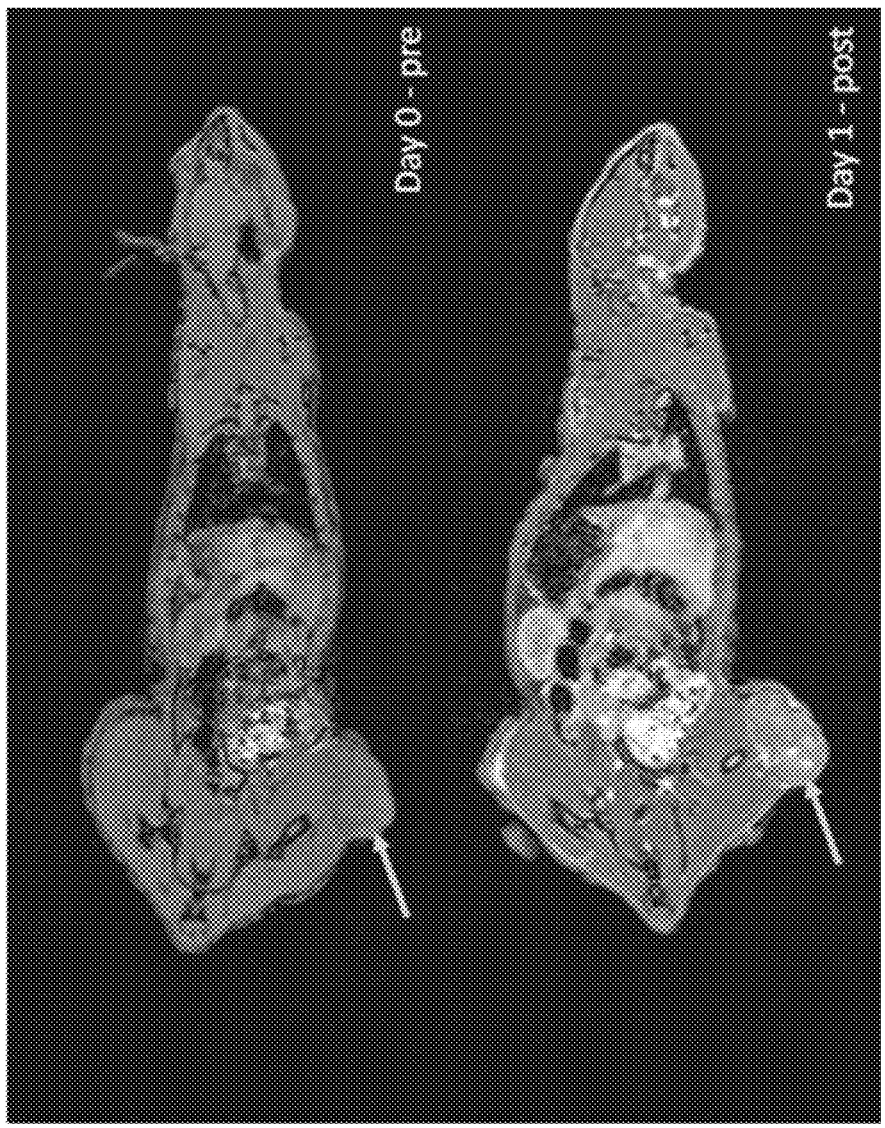
FIG. 18 shows T1-weighted scans of a U87 flank xenograft bearing rat using a clinical 3.0 T PET/MR. Rats were imaged pre- and 24 hours post-administration of Gd-DO3A-404.

T1-weighted scans of the U87 flank xenograft were obtained using the clinical 3.0 T PET/MR. Rats were imaged pre- and 24 hours post-administration of the Gd-DO3A-404. The resulting MR images demonstrate selective tumor uptake of the Gd-DO3A-404 contrast agent (FIG. 18; arrow showing tumor location).

Figure 19:
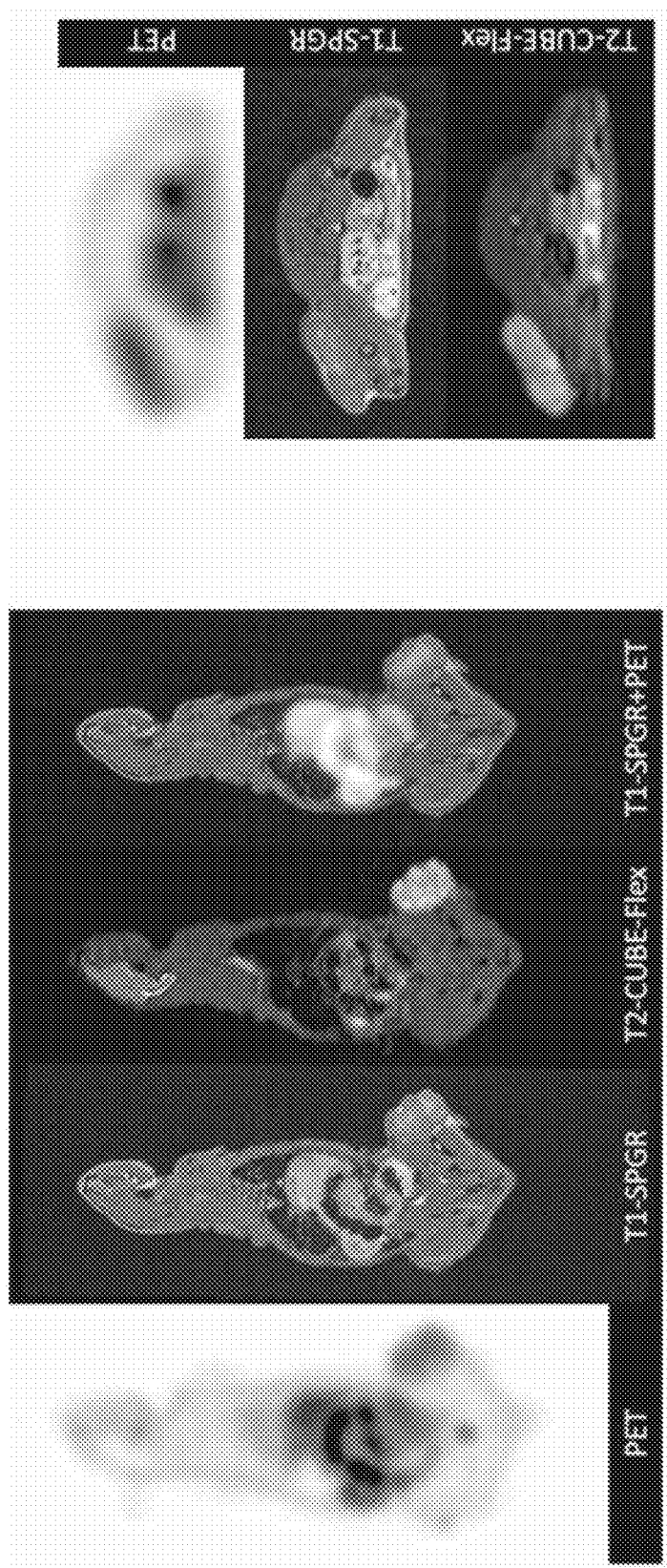
FIG. 19 shows simultaneous PET/MR images of a U87-flank bearing rat 24 hours post-administration of Gd-DO3A-404 and Cu-DO3A-404. Gd-DO3A-404 and 64Cu-DO3A-404 and were simultaneously administered to a U87-flank bearing rat. The rat was imaged using simultaneous PET/MR. Arrow points to tumor.

Simultaneous PET/MR scans of the U87-flank bearing rat 24 hours post-simultaneous administration of both Gd-DO3A-404 (the MRI contrast agent) and $^{64}$Cu-DO3A-404 (the PET contrast agent) were obtained. As seen in FIG. 19, fused T1-weighted MR and PET images showed excellent colocalization of contrast and activity in the flank and abdomen (arrow points to tumor). The tumor is enhanced enhances in both the T1 and T2 MRI images (FIG. 19). Furthermore, the simultaneous PET scan demonstrates tumor uptake of the $^{64}$Cu-DO3A-404 PET contrast agent (FIG. 19), providing proof-of concept for using the disclosed chelates having a radioactive metal substituted for Gd in tumor imaging (such as PET imaging) and radiotherapy applications.

In sum, these examples demonstrate that radioactive metal chelates that include an appropriate tumor-targeting phospholipid moiety, as disclosed herein, would demonstrate selective uptake and retention in multiple cancer types. Such chelates will facilitate improved detection, characterization, and staging of cancer and metastases. In addition, such agents can be used for radiotherapy targeted to the solid tumors in which they are selectively taken up and retained.

Other embodiments and uses of the invention will be apparent to those skilled in the art from consideration from the specification and practice of the invention disclosed herein. All references cited herein for any reason, including all journal citations and U.S./foreign patents and patent applications, are specifically and entirely incorporated herein by reference. It is understood that the invention is not confined to the specific reagents, formulations, reaction conditions, etc., herein illustrated and described, but embraces such modified forms thereof as come within the scope of the following claims.

The invention claimed is:

1. A method for treating a cancer in a subject, comprising administering to a subject having cancer an effective amount of a compound having the formula:

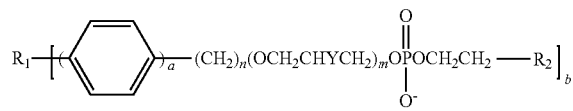

or a salt thereof, wherein:

$R_1$ comprises a chelating agent that is chelated to a metal atom, wherein the metal atom is an alpha, beta or Auger emitting metal isotope with a half life of greater than 6 hours and less than 30 days;

a is 0 or 1;

n is an integer from 12 to 30;

m is 0 or 1;

Y is selected from the group consisting of —H, —OH, —COOH, —COOX, —OCOX, and —OX, wherein X is an alkyl or an arylalkyl;

$R_2$ is selected from the group consisting of —N$^+$H$_3$, —N$^+$HZ$_2$, —N$^+$HZ$_2$, and —N$^+$Z$_3$, wherein each Z is independently an alkyl or an aroalkyl; and b is 1 or 2;

whereby the cancer is successfully treated in the subject.

2. The method of claim 1, wherein the metal isotope is selected from the group consisting of Lu-177, Y-90, Ho-166, Re-186, Re-188, Cu-67, Au-199, Rh-105, Ra-223, Ac-225, As-211, Pb-212, and Th-227.

3. The method of claim 1, wherein the chelating agent is selected from the group consisting of 1,4,7,10-tetraazacyclododecane-1,4,7-triacetic acid (DO3A) and its derivatives; 1,4,7-triazacyclononane-1,4-diacetic acid (NODA) and its derivatives; 1,4,7-triazacyclononane-1,4,7-triacetic acid (NOTA) and its derivatives; 1,4,7,10-tetraazacyclododecane-1,4,7,10-tetraacetic acid (DOTA) and its derivatives; 1,4,7-triazacyclononane,1-glutaric acid-4,7-diacetic acid (NODAGA) and its derivatives; 1,4,7,10-tetraazacyclodecane, 1-glutaric acid-4,7,10-triacetic acid (DOTAGA) and its derivatives; 1,4,8,11-tetraazacyclotetradecane-1,4,8,11-tetraacetic acid (TETA) and its derivatives; 1,4,8,11-tetraazabicyclo[6.6.2]hexadecane-4,11-diacetic acid (CB-TE2A) and its derivatives; diethylene triamine pentaacetic acid (DTPA), its diester, and its derivatives; 2-cyclohexyl diethylene triamine pentaacetic acid (CHX-A"-DTPA) and its derivatives; deforoxamine (DFO) and its derivatives; 1,2[[6-carboxypyridin-2-yl]methylamino]ethane (H$_2$dedpa) and its derivatives; and DADA and its derivatives.

4. The method of claim 1, wherein the chelating agent chelated to the metal atom is selected from the group consisting of:

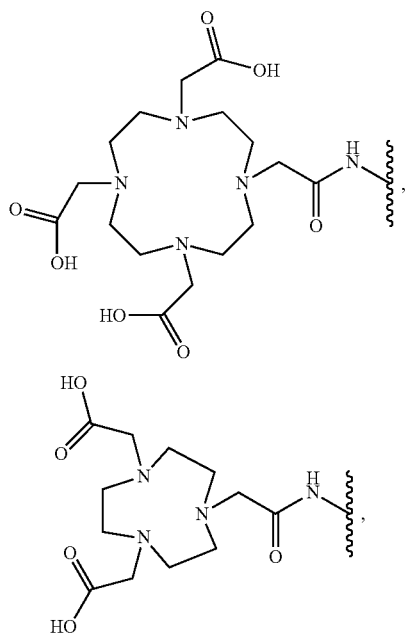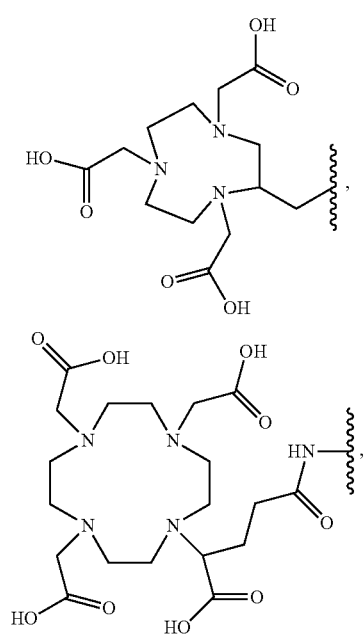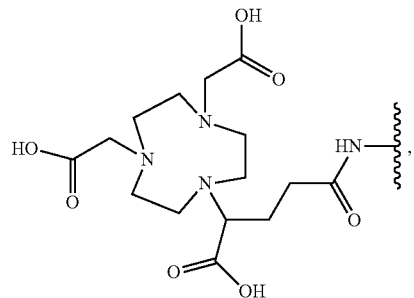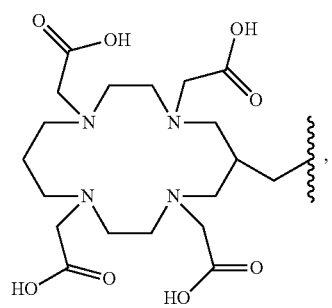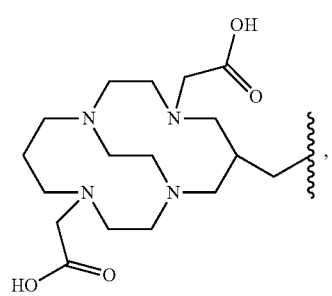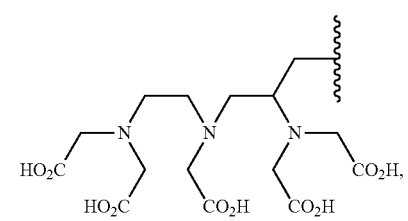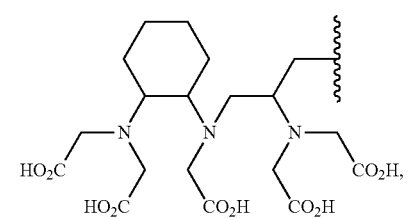

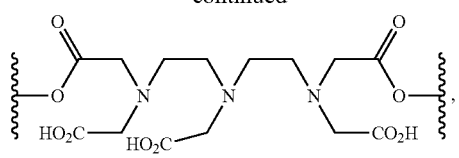
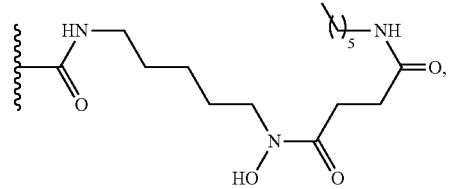
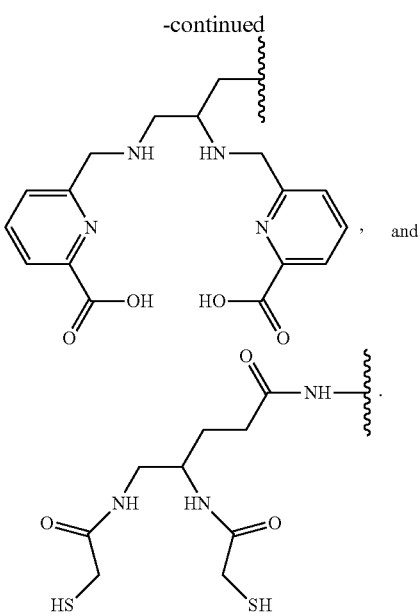
5. The method of claim 1, wherein the compound is selected from the group consisting of:
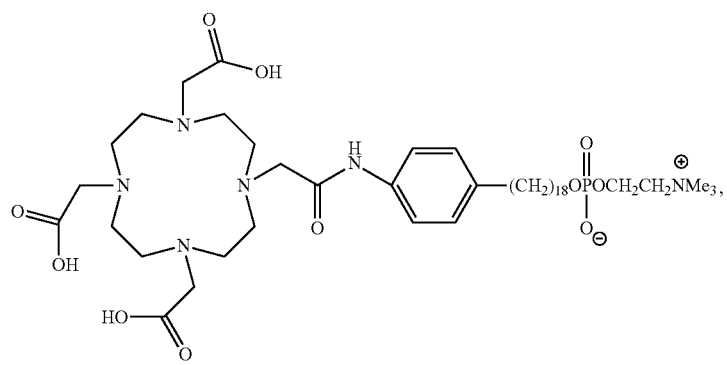
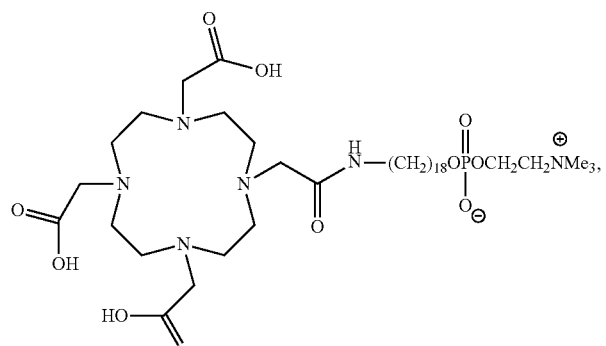
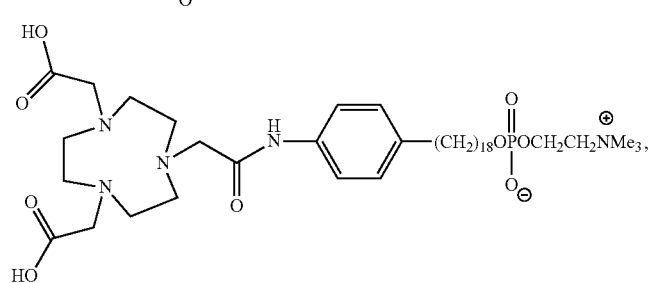

-continued
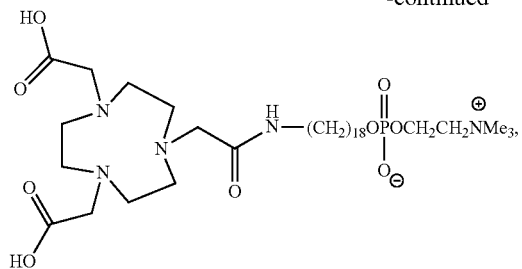
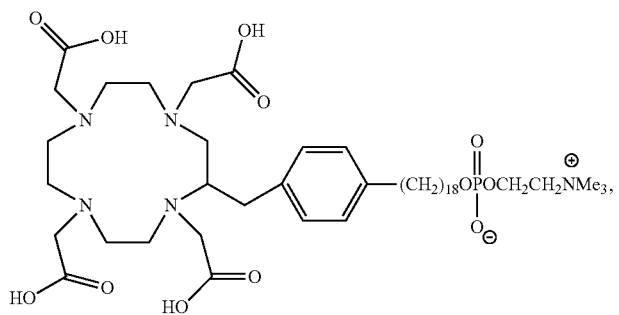
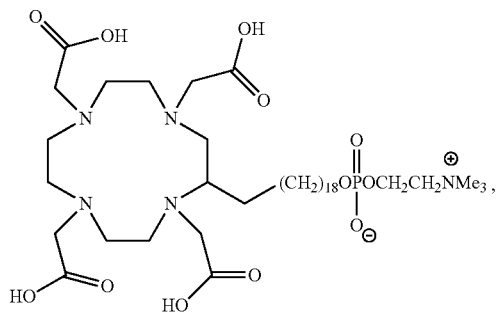
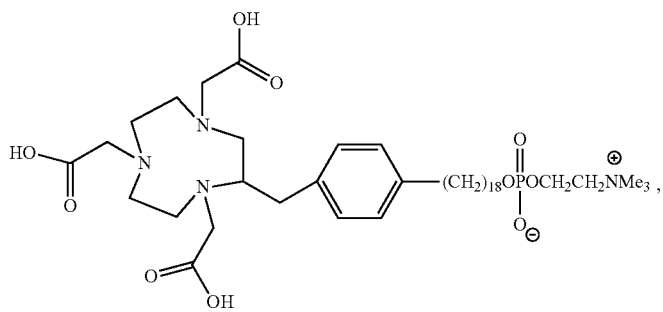
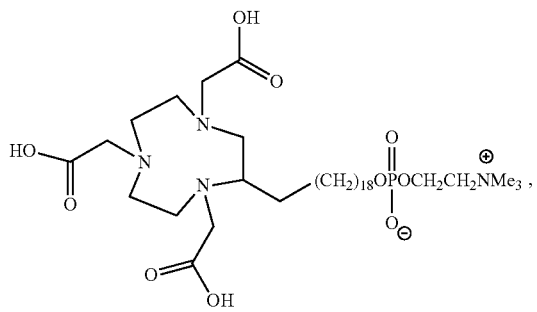

-continued
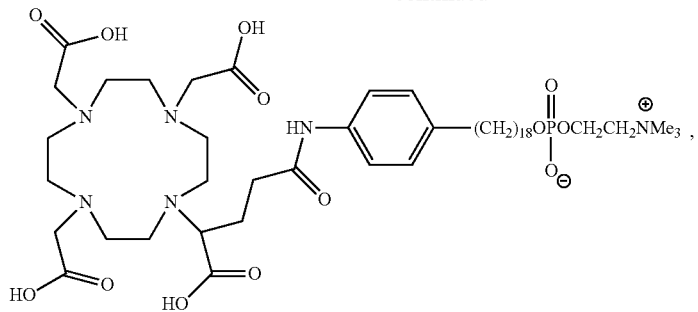
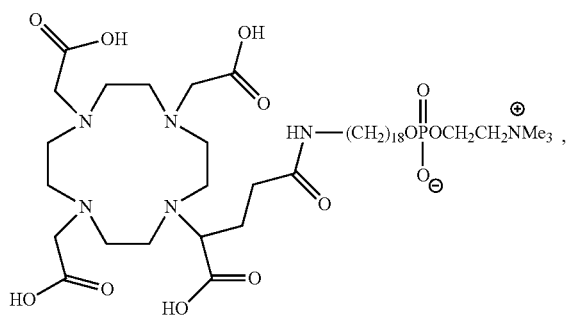
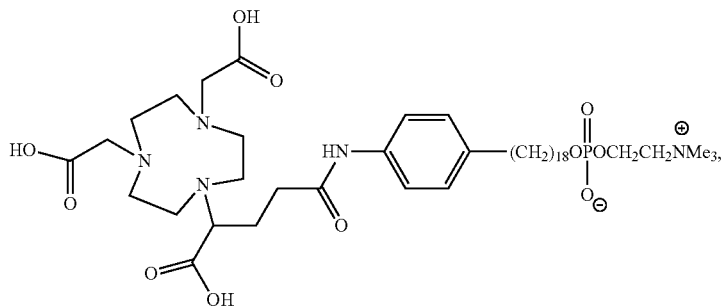
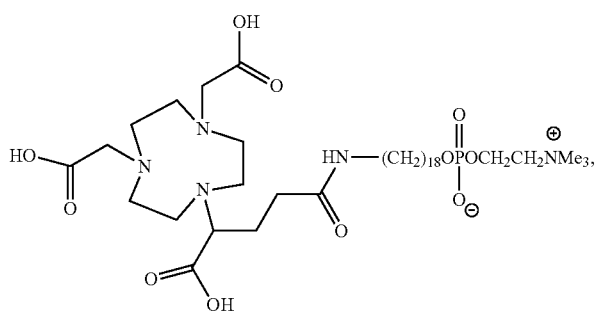
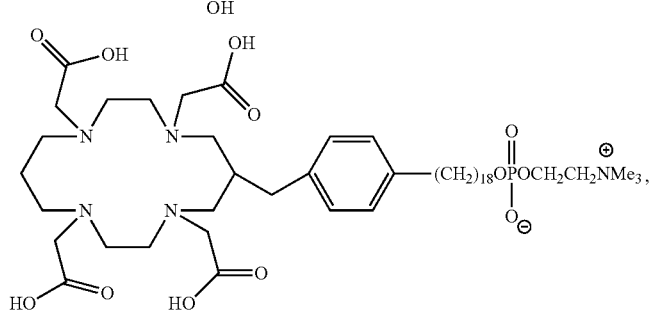

-continued
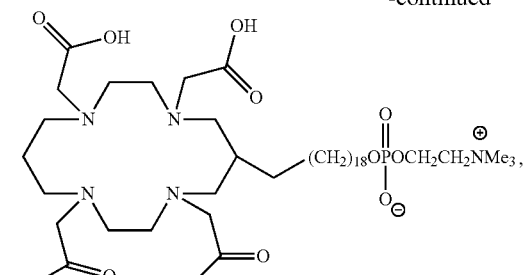
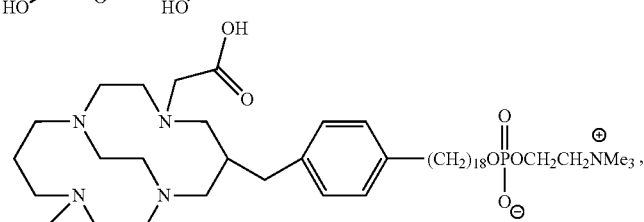
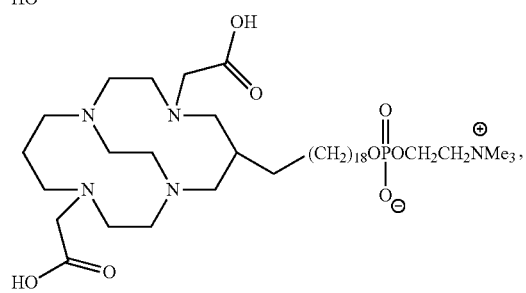
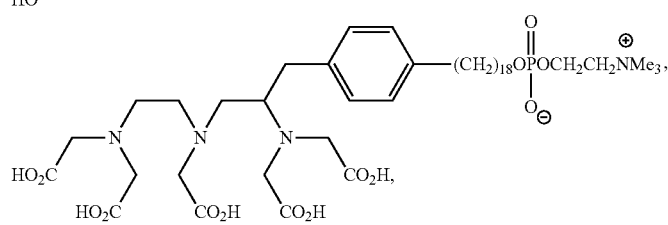
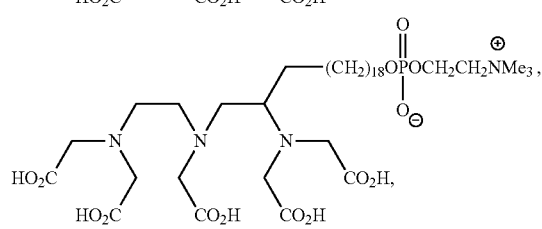
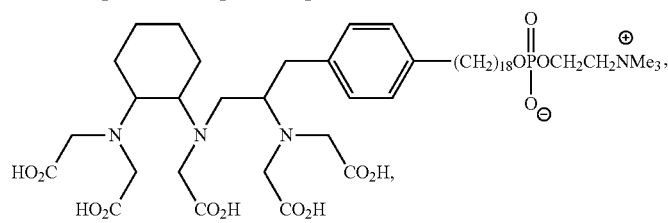
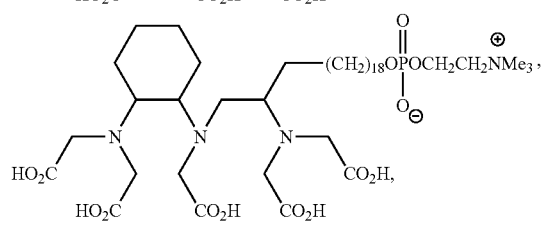

-continued
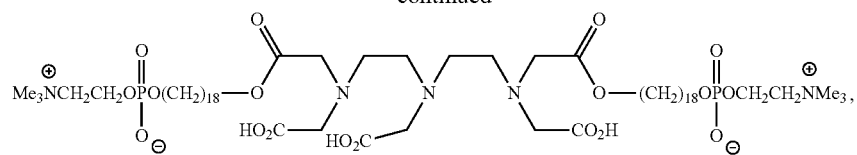
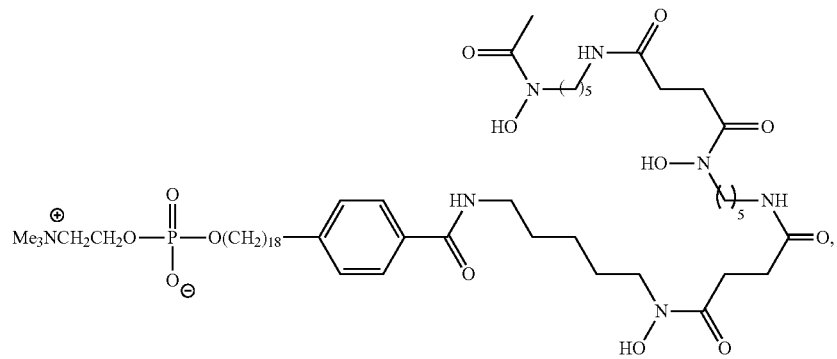
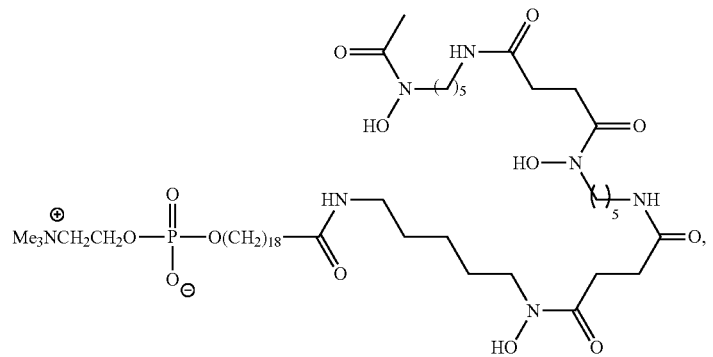
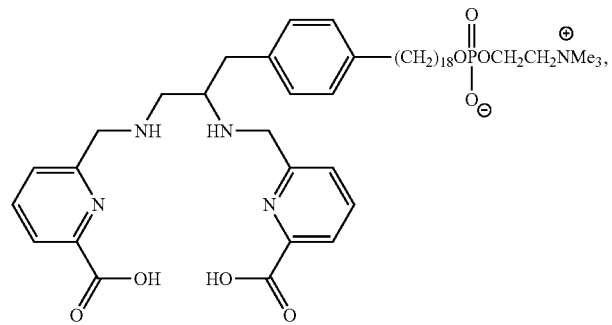
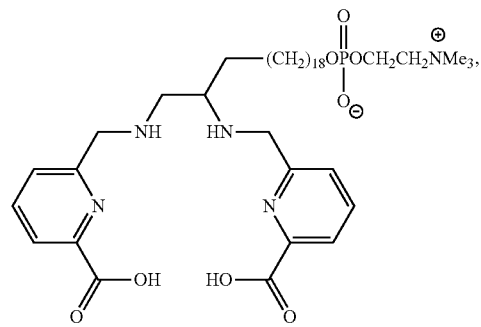

-continued

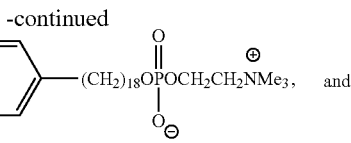

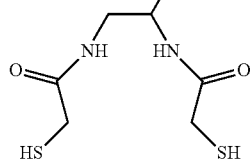

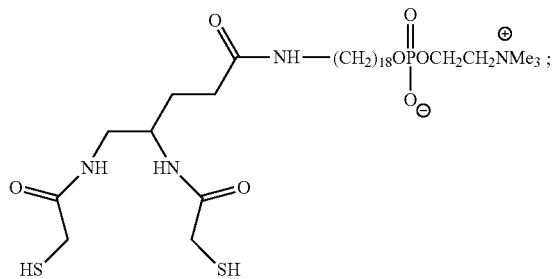

wherein the selected compound is chelated to the metal atom.

6. The method of claim 1, wherein the subject is a human.

7. The method of claim 1, wherein the cancer that is treated is an adult solid tumor or a pediatric solid tumor.

8. The method of claim 7, wherein the cancer is selected from the group consisting of melanoma, neuroblastoma, lung cancer, adrenal cancer, colon cancer, colorectal cancer, ovarian cancer, prostate cancer, liver cancer, subcutaneous cancer, squamous cell cancer, intestinal cancer, retinoblastoma, cervical cancer, glioma, breast cancer, pancreatic cancer, Ewings sarcoma, rhabdomyosarcoma, osteosarcoma, retinoblastoma, Wilms' tumor, and pediatric brain tumors.

9. A method for detecting or imaging one or more cancer cells in a biological sample, comprising:
(a) contacting the biological sample with a compound having the formula:

or a salt thereof, wherein:
$R_1$ comprises a chelating agent that is chelated to a metal atom, wherein the metal atom is a positron or single photon emitting metal isotope with a half life of greater than or equal to 4 hours;
a is 0 or 1;
n is an integer from 12 to 30;
m is 0 or 1;
Y is selected from the group consisting of —H, —OH, —COOH, —COOX, —OCOX, and —OX, wherein X is an alkyl or an arylalkyl;
$R_2$ is selected from the group consisting of —$N^+H_3$, —$N^+H_2Z$, —$N^+HZ_2$, and —$N^+Z_3$, wherein each Z is independently an alkyl or an aroalkyl; and
b is 1 or 2;

whereby the compound is differentially taken up by malignant solid tumor cells within the biological sample; and
(b) identifying individual cells or regions within the biological sample that are emitting signals characteristic of the metal isotope, whereby one or more cancer cells are detected or imaged.

10. The method of claim 9, wherein the metal isotope is selected from the group consisting of Ga-66, Cu-64, Y-86, Co-55, Zr-89, Sr-83, Mn-52, As-72, Sc-44, Ga-67, In-111, and Tc-99m.

11. The method of claim 9, wherein the step of identifying individual cells or regions within the biological sample that are emitting signals characteristic of the metal isotope is performed by positron emission tomography (PET) imaging, single-photon emission computed tomography (SPECT) imaging, or gamma camera planar imaging.

12. The method of claim 9, wherein the chelating agent is selected from the group consisting of 1,4,7,10-tetraazacyclododecane-1,4,7-triacetic acid (DO3A) and its derivatives; 1,4,7-triazacyclononane-1,4-diacetic acid (NODA) and its derivatives; 1,4,7-triazacyclononane-1,4,7-triacetic acid (NOTA) and its derivatives; 1,4,7,10-tetraazacyclododecane-1,4,7,10-tetraacetic acid (DOTA) and its derivatives; 1,4,7-triazacyclononane,1-glutaric acid-4,7-diacetic acid (NODAGA) and its derivatives; 1,4,7,10-tetraazacyclodecane, 1-glutaric acid-4,7,10-triacetic acid (DOTAGA) and its derivatives; 1,4,8,11-tetraazacyclotetradecane-1,4,8,11-tetraacetic acid (TETA) and its derivatives; 1,4,8,11-tetraazabicyclo[6.6.2]hexadecane-4,11-diacetic acid (CB-TE2A) and its derivatives; diethylene triamine pentaacetic acid (DTPA), its diester, and its derivatives; 2-cyclohexyl diethylene triamine pentaacetic acid (CHX-A"-DTPA) and its derivatives; deforoxamine (DFO) and its derivatives; 1,2-[[6-carboxypyridin-2-yl]methylamino]ethane ($H_2$dedpa) and its derivatives; and DADA and its derivatives.

13. The method of claim 9, wherein the chelating agent chelated to the metal atom is selected from the group consisting of:

55
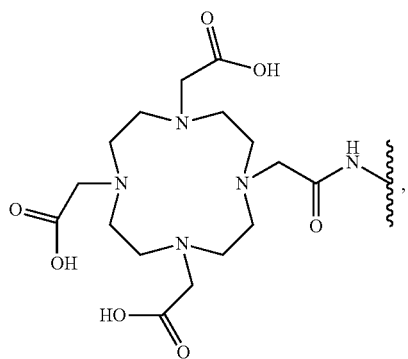
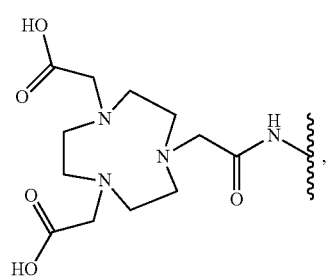
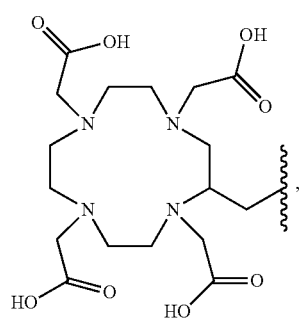
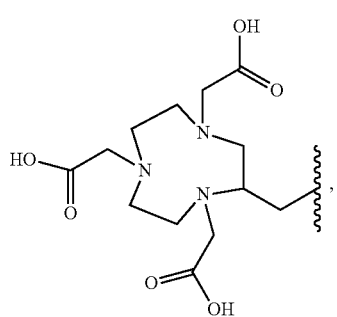
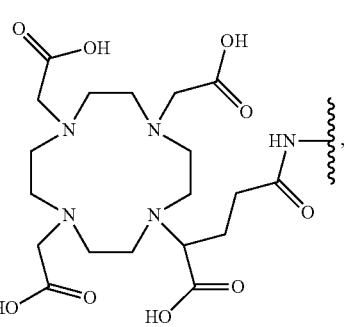
56
-continued
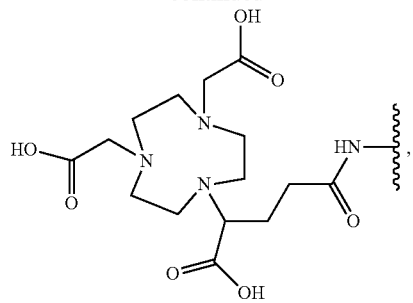
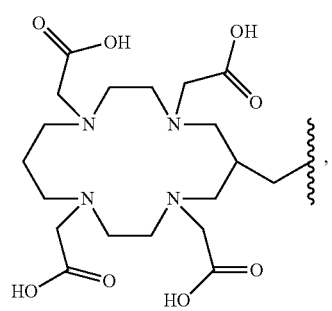
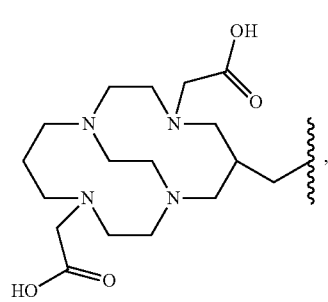
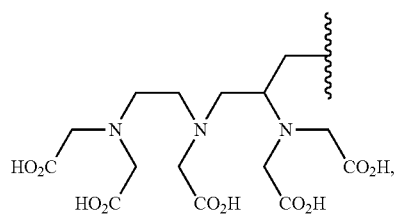
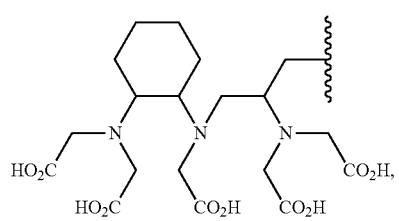

57
-continued
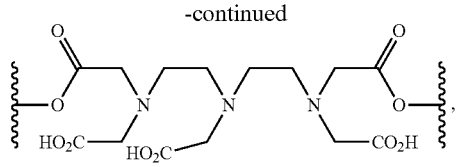
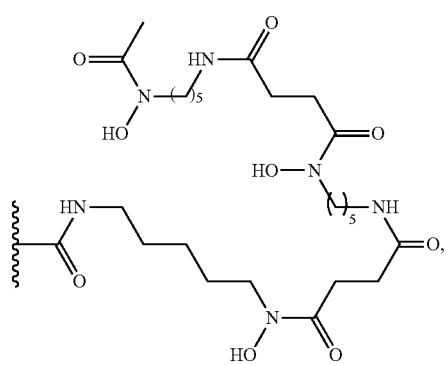
58
-continued
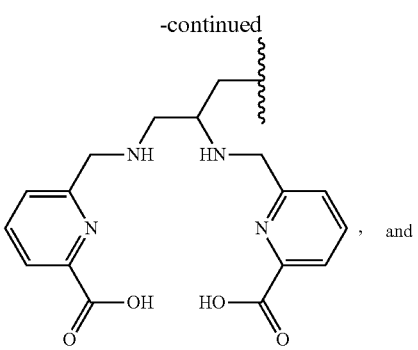, and
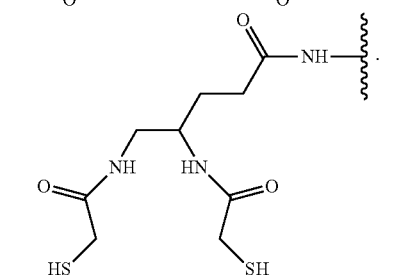.
14. The method of claim 9, wherein the compound is selected from the group consisting of:
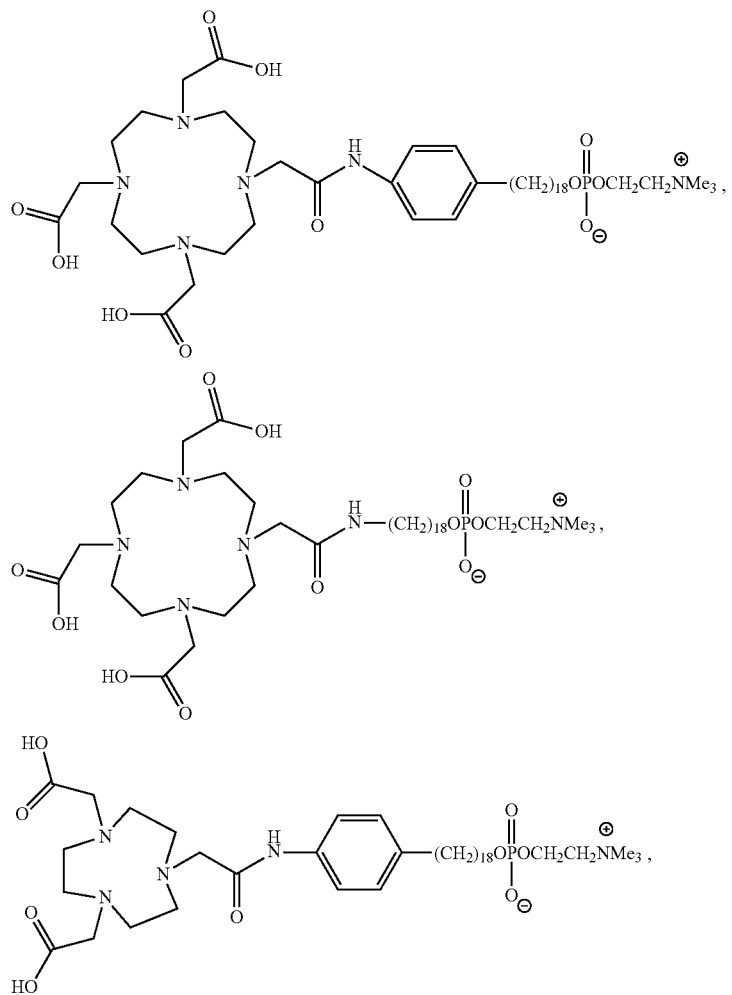

-continued
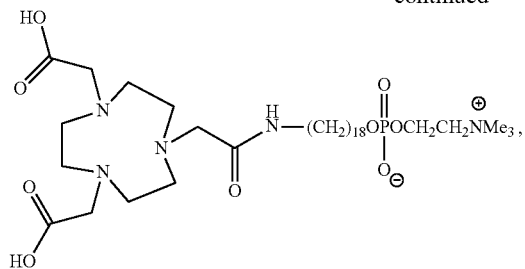
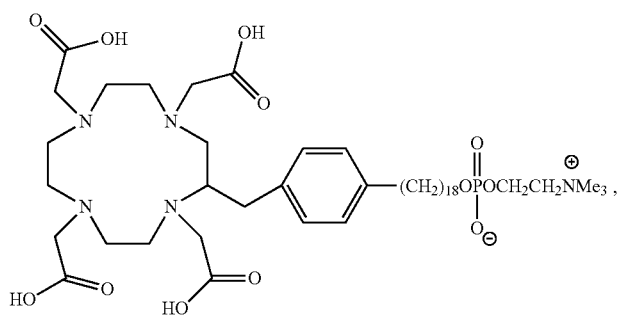
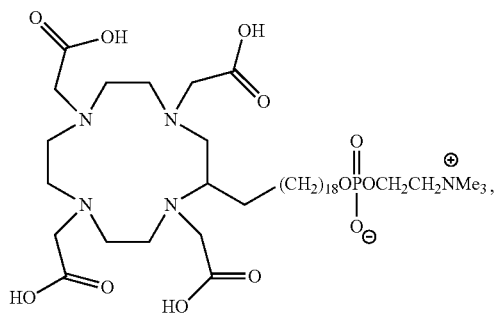
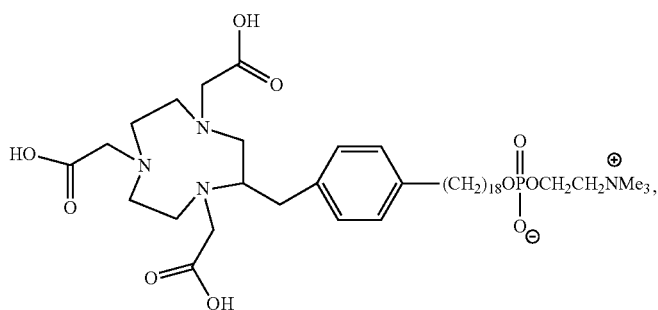
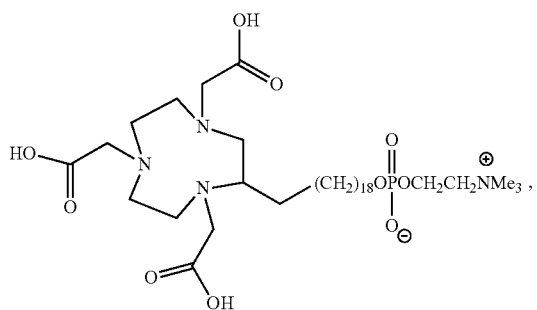

-continued
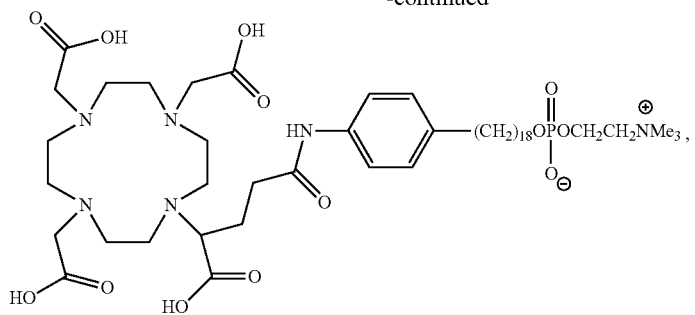
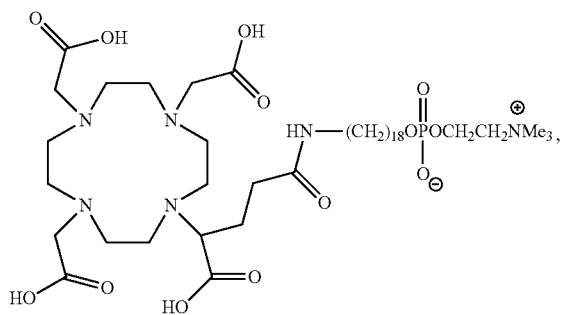
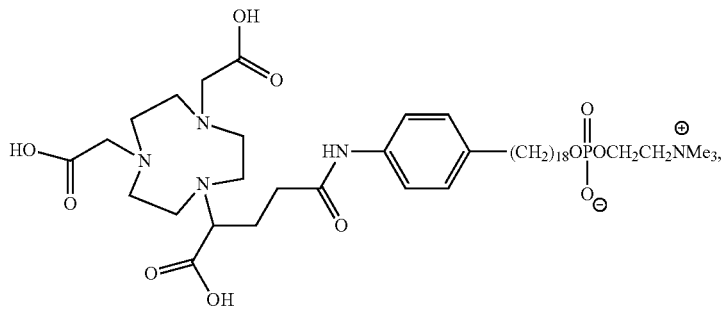
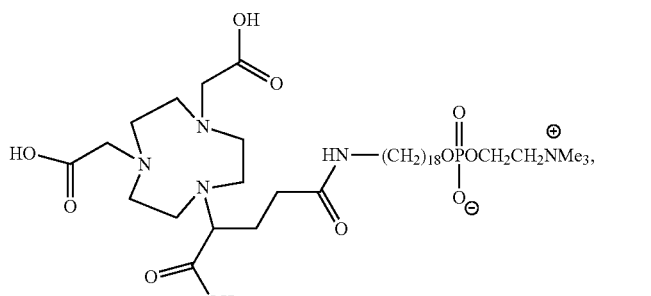
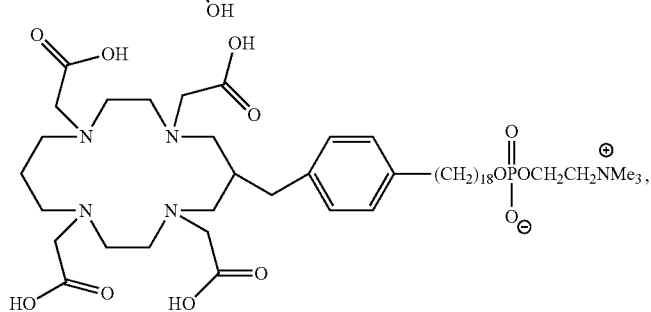

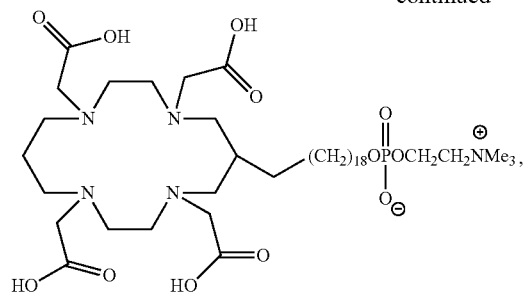
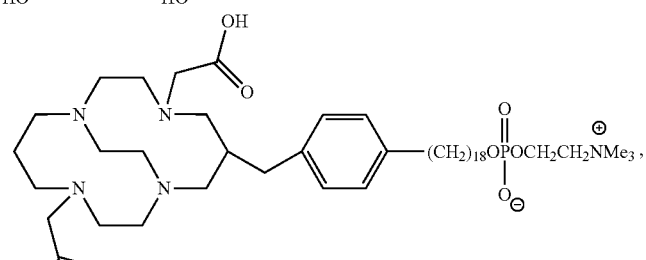
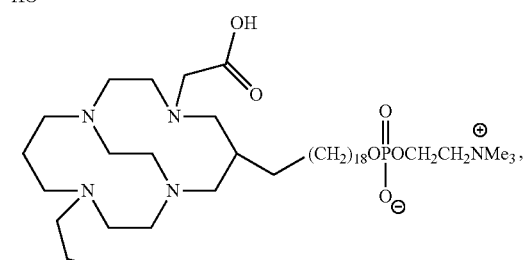
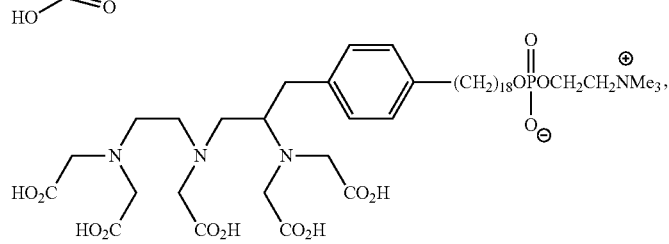
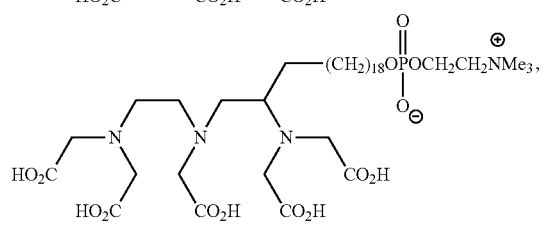
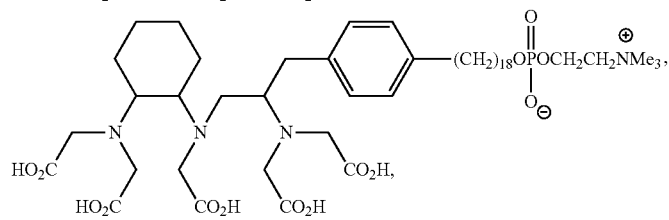
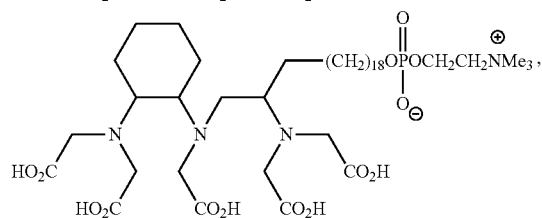

-continued
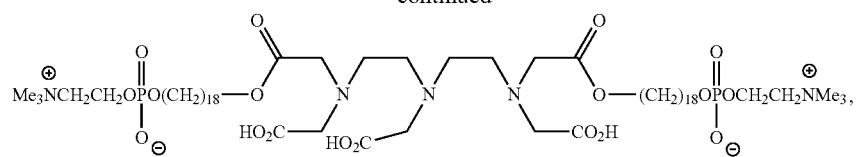
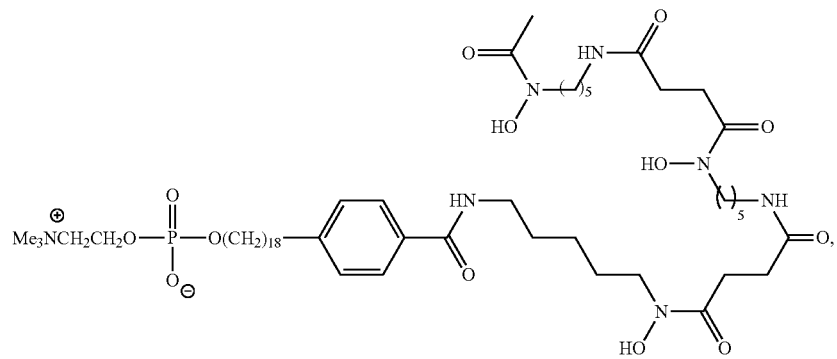
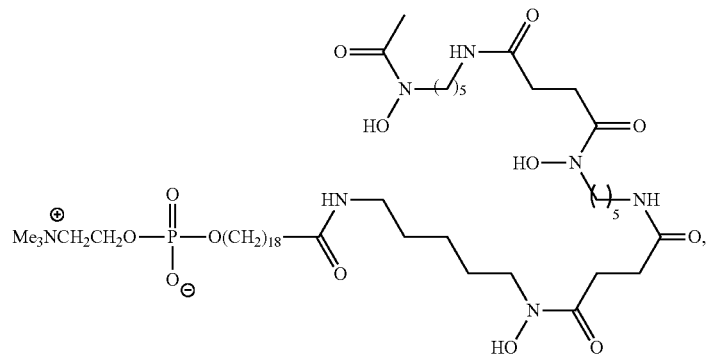
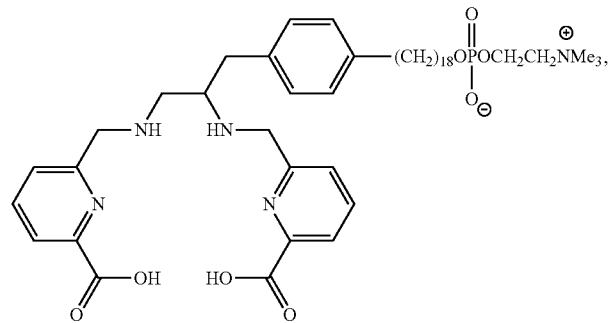
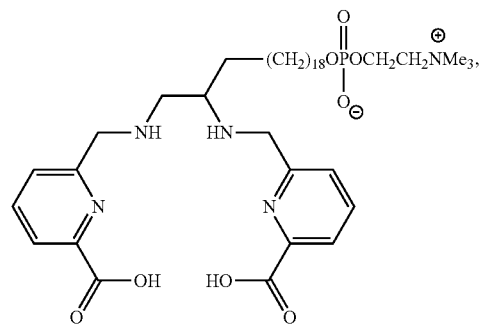

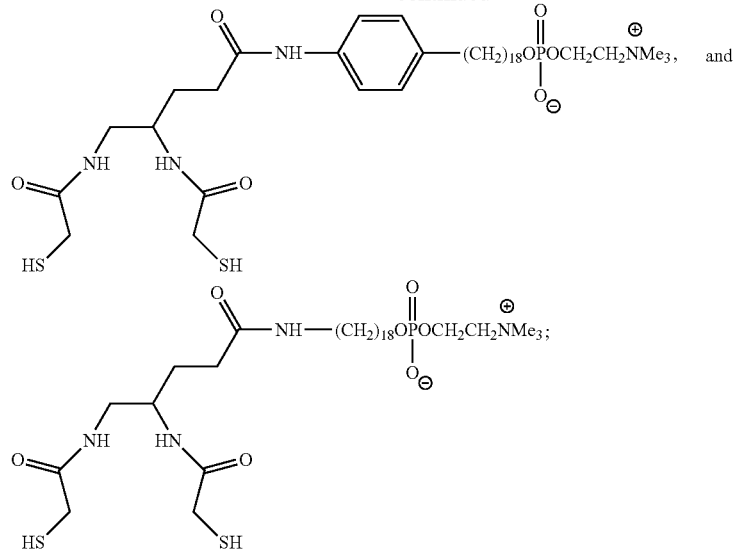

wherein the selected compound is chelated to the metal atom.

15. The method of claim 9, wherein the biological sample is part or all of a subject.

16. The method of claim 15, wherein the subject is a human.

17. The method of claim 9, wherein the cancer cells are adult solid tumor cells or pediatric solid tumor cells.

18. The method of claim 17, wherein the cancer cells are selected from the group consisting of melanoma cells, neuroblastoma cells, lung cancer cells, adrenal cancer cells, colon cancer cells, colorectal cancer cells, ovarian cancer cells, prostate cancer cells, liver cancer cells, subcutaneous cancer cells, squamous cell cancer cells, intestinal cancer cells, retinoblastoma cells, cervical cancer cells, glioma cells, breast cancer cells, pancreatic cancer cells, Ewings sarcoma cells, rhabdomyosarcoma cells, osteosarcoma cells, retinoblastoma cells, Wilms' tumor cells, and pediatric brain tumor cells.

19. A method of diagnosing cancer in a subject, comprising performing the method of claim 9, wherein the biogical sample is obtained from, part of, or all of a subject, and whereby if cancer cells are detected or imaged, the subject is diagnosed with cancer.

* * * * *

UNITED STATES PATENT AND TRADEMARK OFFICE
CERTIFICATE OF CORRECTION

PATENT NO. : 11,186,598 B2
APPLICATION NO. : 16/891181
DATED : November 30, 2021
INVENTOR(S) : Weichert et al.

It is certified that error appears in the above-identified patent and that said Letters Patent is hereby corrected as shown below:

In the Specification

Under STATEMENT REGARDING FEDERALLY SPONSORED RESEARCH OR DEVELOPMENT please replace "Not applicable." with the following:
-- This invention was made with government support under CA250972, CA233102 and CA014520 awarded by the National Institutes of Health. The government has certain rights in the invention. --

Signed and Sealed this
Seventh Day of June, 2022

Katherine Kelly Vidal
*Director of the United States Patent and Trademark Office*